(12) United States Patent
Dehn

(10) Patent No.: US 8,844,158 B2
(45) Date of Patent: Sep. 30, 2014

(54) SUPER ABSORBER POLYMER FELT AND METHOD FOR THE PRODUCTION THEREOF

(75) Inventor: Michael Christian Dehn, Hamburg (DE)

(73) Assignee: IQTEX Patentverwaltung UG, Hamburg (DE)

( * ) Notice: Subject to any disclaimer, the term of this patent is extended or adjusted under 35 U.S.C. 154(b) by 436 days.

(21) Appl. No.: 13/140,439

(22) PCT Filed: Dec. 18, 2009

(86) PCT No.: PCT/EP2009/009143
§ 371 (c)(1),
(2), (4) Date: Sep. 21, 2011

(87) PCT Pub. No.: WO2010/069592
PCT Pub. Date: Jun. 24, 2010

(65) Prior Publication Data
US 2012/0036733 A1    Feb. 16, 2012

(30) Foreign Application Priority Data

Dec. 19, 2008  (DE) .......................... 10 2008 063 229
Feb. 20, 2009  (EP) ..................................... 09002419

(51) Int. Cl.
*F26B 5/06*      (2006.01)
*A61F 13/00*    (2006.01)
*A61F 13/537*   (2006.01)
*D04H 1/42*     (2012.01)
*B32B 5/26*     (2006.01)
*D04H 1/407*    (2012.01)
*A61F 13/15*    (2006.01)
*D04H 13/00*    (2006.01)
*D04H 1/4374*   (2012.01)
*A61F 13/539*   (2006.01)
*A61F 13/535*   (2006.01)
*A61F 13/538*   (2006.01)
*A61L 15/60*    (2006.01)
*D04H 1/498*    (2012.01)
*A61F 13/53*    (2006.01)

(52) U.S. Cl.
CPC ........... *A61L 15/60* (2013.01); *A61F 13/00008* (2013.01); *A61F 13/53704* (2013.01); *D04H 1/42* (2013.01); *B32B 5/26* (2013.01); *D04H 1/407* (2013.01); *A61F 13/15658* (2013.01); *A61F 2013/00744* (2013.01); *A61F 2013/530532* (2013.01); *D04H 13/00* (2013.01); *A61F 2013/530547* (2013.01); *D04H 1/4374* (2013.01); *A61F 13/539* (2013.01); *A61F 13/535* (2013.01); *A61F 13/53713* (2013.01); *A61F 13/53756* (2013.01); *A61F 13/00046* (2013.01); *A61F 2013/00544* (2013.01); *A61F 13/53717* (2013.01); *A61F 13/00029* (2013.01); *A61F 2013/00748* (2013.01); *A61F 13/538* (2013.01); *A61F 2013/00246* (2013.01); *A61F 2013/530554* (2013.01); *D04H 1/498* (2013.01); *A61F 13/53747* (2013.01)
USPC ........ 34/381; 34/413; 34/95; 34/282; 34/105; 156/305; 428/332; 405/109; 442/334

(58) Field of Classification Search
USPC ............. 34/282, 95, 381, 104, 105, 413, 444; 156/71, 148, 305; 428/213, 332; 405/107, 109; 442/268, 325, 334
See application file for complete search history.

(56) References Cited

U.S. PATENT DOCUMENTS

| | | | |
|---|---|---|---|
| 3,607,591 | A | 9/1971 | Hansen |
| 4,424,248 | A * | 1/1984 | Tesch et al. .................. 428/172 |
| 4,495,235 | A * | 1/1985 | Tesch ........................... 428/137 |
| 4,640,810 | A | 2/1987 | Laursen |
| 4,662,874 | A | 5/1987 | Korpman |
| 4,994,053 | A | 2/1991 | Lang |
| 5,041,330 | A * | 8/1991 | Heerten et al. ................ 428/213 |
| 5,174,231 | A * | 12/1992 | White ........................... 112/420 |
| 5,296,290 | A | 3/1994 | Brassington |
| 5,346,565 | A * | 9/1994 | White ........................... 156/71 |
| 5,346,566 | A * | 9/1994 | White ........................... 156/71 |
| 6,420,625 | B1 | 7/2002 | Jones |
| 6,767,850 | B1 | 7/2004 | Tebbe |
| 2004/0049942 | A1 | 3/2004 | Chen |
| 2006/0021695 | A1 | 2/2006 | Blessing |
| 2006/0149197 | A1 | 7/2006 | Niemeyer |
| 2008/0249492 | A1 | 10/2008 | Schmidt |
| 2009/0203275 | A1 | 8/2009 | Dehn |
| 2012/0036733 | A1 * | 2/2012 | Dehn ............................. 34/282 |

FOREIGN PATENT DOCUMENTS

| | | |
|---|---|---|
| CH | 629 137 | 4/1982 |
| DE | 32 44 386 | 6/1984 |
| DE | 3244386 | 6/1984 |
| DE | 37 04 503 | 8/1988 |
| DE | 196 18 858 | 11/1997 |
| DE | 698 33 007 | 3/1999 |
| DE | 20 2004 000307 | 5/2000 |
| DE | 10 2006 042 145 | 10/2007 |
| DE | 10 2007 016 959 | 10/2008 |
| EP | 0 278 419 | 8/1988 |
| EP | 0 491 454 | 6/1992 |
| EP | 0 491 454 | 12/1992 |
| EP | 1 054 095 | 11/2000 |
| GB | 2 377 177 | 1/2003 |
| WO | WO 91/01766 | 2/1991 |
| WO | WO 00/04936 | 2/2000 |
| WO | WO 2004/016425 | 2/2004 |
| WO | WO-2005/095692 | 10/2005 |

OTHER PUBLICATIONS

PCT International Search Report, dated Mar. 8, 2010, issued in parallel application PCT/EP2009/009143, 6 pages.
PCT International Preliminary Report on Patentability, dated Jun. 21, 2011, issued in parallel application, PCT/EP2009/009143, 14 pages.
DIAPLEX:"What's So Intelligent" Internet Article XP002409993, from internet: URL: http://web.archive.org/web/199991202002110/http://www.diaplex.com/intelligent.html (Dec. 2, 1999).
Office Action dated Mar. 22, 2012, in U.S. Appl. No. 11/911,593 (US Published appln. US 2009/0297756).
Office Action dated Jul. 26, 2012, in U.S. Appl. No. 11/911,593 (US Published appln. US 2009/0297756).
Office Action dated Aug. 8, 2013, in U.S. Appl. No. 11/911,593 (US Published appln. US 2009/0297756).
Office Action dated Nov. 15, 2011, in U.S. Appl. No. 12/310,696 (US Published appln. US 2009/0203275).
Office Action dated Jun. 12, 2012, in U.S. Appl. No. 12/310,696 (US Published appln. US 2009/0203275).

\* cited by examiner

*Primary Examiner* — Steve M Gravini
(74) *Attorney, Agent, or Firm* — Nash and Titus, LLC

(57) ABSTRACT

The invention relates to a felt material comprising at least one felt layer and an absorbing layer, to a method for producing the felt material, and to the use of the felt material in textiles, shoes, technical application or medical applications. The felt material according to the invention has the advantages of conventional felt materials regarding the warming and damping properties and is permeable to air in the dry state. Due to the special design, however, it is waterproof in the wet state and thus it is suitable for sealing many materials. The felt material according to the invention binds more humidity or binds water in a different way than common felt materials.

35 Claims, 3 Drawing Sheets

US 8,844,158 B2

SUPER ABSORBER POLYMER FELT AND METHOD FOR THE PRODUCTION THEREOF

BACKGROUND OF THE INVENTION

This application is a 371 national filing claiming priority from international application PCT/EP2009/009143, filed Dec. 18, 2009. This application also claims priority from German application DE 10 2008 063 229.5, filed Dec. 19, 2008, and from European application EP 09 002 419.1, filed Feb. 20, 2009. The entire contents of that international application and that German application and that European application are incorporated herein by reference.

The object of the present invention is a felt material with a barrier function comprising at least one felt layer and an absorber containing material, as well as a method for the production of the felt material, a component made of this felt material and its use.

Felt is a fabric for textiles which has a sheet-like structure and which consists of mechanically bonded fibers. Unlike other fabrics, felt is not woven. Instead, it is manufactured under the influence exerted by pressure with the procedure for pressed felts, or by using an acid to roughen the fibers and to create a nonwoven fabric which is bonded by moisture and heat. Traditionally, pressed felts are made from wool or from other loose animal hair because due to the peeling structure of the hair, the fibers become mutually entangled. The hardness of the felt can range between that of soft cotton or of hard wood, and felts which have even a higher hardness can be also produced. The classical wool felts are also referred to as pressed or milling felts.

More recently, felts have been often produced as needle felts. In this case, the fibers are placed in layers on top of each other and processed with numerous needles which are provided with barbs so that they are pierced through several times. The repeated insertion of the fibers means that they are intertwined or pressed in the felt. The needle felts can be therefore manufactured not only from wool, but virtually from all known fibers.

Due to its warming properties, felt is used also for the manufacture of clothing, lining materials or shoes, as well as for insulating materials. They are particularly popular due to their warming effect, for example when used in shoes made of felts, or in felt hats or cardigans. In technology, felts are used for example for sealing materials made of felts, felt rings or felt strips, or as surface materials for sealing or soundproofing. In addition, technical molded parts or filters made from felt materials are also known. In addition to its heat insulating characteristics, felt is also permeable to air and to a certain extent it is waterproof. However, with a larger amount of water, for example when it rains, water will penetrate through the felt.

The felt material feels uncomfortable and heavy when it is wet because it traps water like a sponge.

In the area of sanitary pads or materials that are used for pillows, it is known that coating materials with super absorbent polymers can be used to absorb water and moisture. For example DE 698 33 007 T2 describes an absorbent product consisting of several layers which is equipped with an absorbent core for absorption of liquids. In order to protect clothing, one of the layers is in this case made from a plastic material, which means that the air permeability of the product is severely limited. The products used in this manner are in this case designed in such a way so as to achieve the maximum absorption of liquids. So far it has not been possible to control the distinct increase of weight and the increased volume of the product caused by this for application to hygienic articles. The large amounts of fluids thus result in correspondingly long drying time periods. In addition, the products are suitable only for single use and they must be disposed of once they have come into contact with fluids. Also, the products are not washable and the superabsorber would be separated from the carrier material as a result of mechanical influences such as during washing in a washing machine, or when it is compressed for a long time.

With respect to hygienic articles, it is further also known from DE 10 2007 016 959 that fiber sheets can be produced from cellulose fibers and that the absorption of these layers which contain cellulose fibers can be improved with the addition of a superabsorber. Also the products described in this document can be used only for disposable articles such as hygienic articles, medical products, diapers, panty liners, articles inserted in food packaging products or disposable filters. The described materials cannot be used in clothing articles or in areas in which repeated use would be required due to the small mechanical strength and also due to the high swelling displayed in case of contact with a fluid. As a result of the large amounts of fluid which are absorbed per surface area, these materials dry out only very slowly because a large volume of fluids must be evaporated. Moreover, the article is also quite heavy due to the large fluid absorption.

SUMMARY OF THE INVENTION

The object of the present invention is therefore to provide an absorbent material which is provided with a high mechanical strength and which in the dry state is provided with a good air permeability. The absorbent material must at the same time display a barrier effect against the penetration of fluids or moisture in the wet or dry status so that at least a significant reduction of the flow through the material is achieved. The objects that are manufactured with these materials must be washable or capable of being cleaned chemically. Furthermore, the absorbent material should be suitable for products that are used for climate regulation, such as for example for ventilation, dehumidification and/or humidification.

Another object of the invention is to provide a simple and inexpensive method for manufacturing such a felt material which can be preferably realized without using special devices.

The objective is achieved in accordance with the invention with a felt layer and with a layer absorbing liquid provided at least in some regions, characterized in that the fluid absorbing layer is an absorbent layer, which contains at least one felt layer that is needled (felted) to an absorbent layer and/or a second felt layer, the absorber is limited in its three-dimensional expansion by the felt layer(s) and/or by locking elements, the felt material is at least partially permeable to air in its dry, opened state and the felt material closes itself when it comes into contact with a fluid, water or water vapor due to the expansion of the absorber, wherein the transport of the fluid through the felt material is limited or stopped by the swollen absorber.

The objective is further achieved with a method for manufacturing a felt material comprising at least one felt layer and at least partially an absorber-containing layer, characterized in that the absorber-containing layer is placed on a felt layer or between two felt layer, and the felt layer(s) and the absorber-containing layer and/or the second felt layer are mutually needled to each other. Other embodiments are described below.

DETAILED DESCRIPTION OF THE PREFERRED EMBODIMENTS

Figure 1:
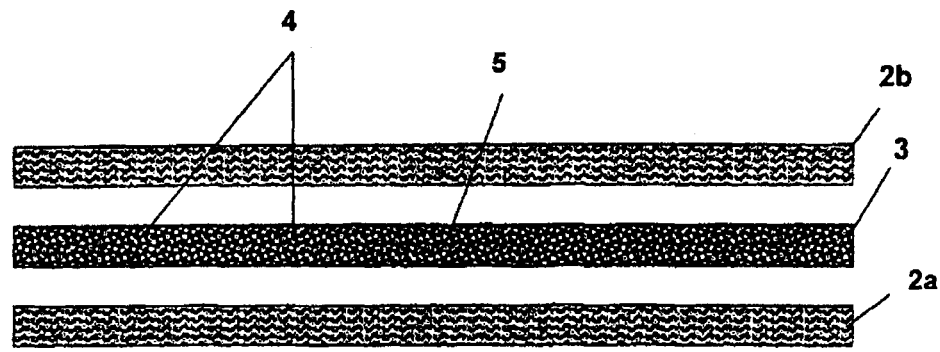
FIG. 1 shows an embodiment of the felt material according to the invention before the felting (entangling) treatment.

The felt material according to the invention is permeable to air in the dry state, so that the ventilation of the article of clothing which is provided with the felt material or of a shoe or other objects can occur. As soon as the felt material according to the invention comes into contact with air or with water vapor (moisture), the enclosed absorber swells up and thus limits the flow through the felt material. In this state which is referred to as a wet state, the felt material is preferably neither permeable to air not to water vapor or other liquids, i.e. it is provided with a barrier function for water/liquids. Under water is understood water in the fluid, aggregate state, while the term water vapor (moisture) refers to water forming gas. Just as contact with water swells up the absorber, so does contact with other liquids, while there are also liquids that cause swelling, as well as inert liquids. The contact with inert liquids does not lead to swelling. At the same time, various absorber polymers, which can be present for example also as an admixture in a felt surface, react differently to water or to certain fluids. Closing of the felt material and thus an activation of the barrier function preferably occurs with contact with water. Contact with water vapor leads either to a slight swelling or with a high absorption density to the closing of the material.

Under filter material according to the invention is understood a flat textile form or structure in which the fibers are mutually entangled with needle felts, or into which the felt is pressed so that optionally and additionally, heating, compression or a chemical reaction is used for solidification. The cohesion in the felt material thus occurs only due to mechanically strengthened and mutually entangled fibers and not by weaving, knitting, sewing or other manufacturing methods.

The filter material according to the invention has the advantage that it is washable, for example when it is employed in articles of clothing, it can be even washed in a normal washing machine, which means that it can be used for the widest range of applications. Thanks to the fact that it is washable, material provided with an absorber polymer can be reused for the first time in various application products. This makes it possible to significantly reduce the waste resulting from the use of disposable products.

Since the felt material according to the invention is provided in various embodiments which have the same characteristics as filter material that is equipped with absorber polymers, the felt material according to the invention can be employed everywhere where normal felt material is also employed. In the dry state, the felt material according to the invention cannot be distinguished from normal needled felt material, either visually or by touch. Therefore, as far as the appearance and the tactile feeling are concerned, a material that is equivalent to conventional material is obtained. However, in comparison to conventional absorber-containing flat materials, the felt material according to the invention display a high mechanical durability and a greater stability.

Surprisingly, the felt material according to the invention can be manufactured with the same machines as needle felts, which is to say that it is not necessary to perform a special adjustment or modification. Therefore, higher processing cost than those that would be required for the production of a normal felt are not generated.

Compared with conventional materials which are provided with superabsorber polymers, such as for example incontinence products known from prior art technology, the felt material of the invention has the advantage that the superabsorber polymers are enclosed in an undetachable manner, which is to say that when the felt material according to the invention is used, parts of the absorber polymer cannot become inadvertently separated from the felt material and thus exert an influence on the application properties.

Another advantage of the felt material according to the invention and of structural components produced from this felt material is that the material is extremely easy to prepare and it can be thus easily adapted to a wide range of applications. In addition, the felt material according to the invention is also provided with a high degree of plasticity so that certain forms and part shapes can be produced in a targeted manner.

In particular due to the washability and the high stability, the felt material according to the invention is characterized by a significantly higher lifespan than functional materials provided with superabsorber polymers.

The material according to the invention differs significantly from known climatic membranes in its air permeability as these membranes are permeable only in one direction and only to water vapor. While it is possible to switch between the permeable and non-permeable state with the felt material according to the invention and air can be transported both from inside to the outside and from outside to the interior, climatic membranes enable transport of water vapor only in one direction of the membrane. Transport of air is not possible with climatic membranes. This represents a significant advantage of the material according to the invention over climatic membranes.

The closing of the filter material occurs due to the limitation of the absorber in its three-dimensional expansion. The absorber is limited in one plane in its expansion by the layers of the felt material. In the two other planes, the absorber is limited in its expansion by the fibers which connect both felt layers and form in this manner small, chamber-like spaces. These fibers are referred to as connecting fibers according to the invention. With the inclusion of the absorber in the felt material, an absorber-containing material is obtained which has a high mechanical strength. This represents a special advantage over known absorber-containing articles in that it allows the felt material according to the invention to be used also in areas in which a high mechanical stress occurs or when multiple use is desired.

The first and the second felt layers are preferably connected together so that the absorber is distributed as evenly as possible and undetachably enclosed by the connecting fibers. The three-dimensional expansion is therefore limited mainly by the connecting fibers between the felt layers, and optionally also by the carrier material.

In another embodiment, the limit can be created in addition to the fibers also by other structures in the edge regions, such as rims made of plastic. Moreover, the absorber is limited in its expansion in one embodiment in addition to the felt fibers also by injections of plastic material or plastic supports into it, such as for example frame elements.

The felt material according to the invention preferably comprises at least three layers, wherein in the first layer is the felt material on which a second layer is arranged consisting of an absorber-containing material, while an additional, second felt layer is arranged on the absorber-containing material. Both felt layers either consist of the same fiber material or they can be made from different fiber materials.

Felt Layer

The felt layer of the felt material according to the invention preferably consists of synthetic, semi-synthetic, animal, mineral, metallic, or vegetable fibers, rubber fibers, hybrid fibers or a mixture thereof. Suitable fibers include for example wool fibers, carbon fibers, microfibers, casein, creatine and synthetic fibers made of polypropylene (PP), polytetrafluoroethylene (PTFE) or polyester (PES). Depending on the embodiment, all the fibers have the same diameter, or at least partially different diameters. Fibers referred to as hybrid fibers are fibers consisting of more than one starting material, for example fibers that are made of different plastic materials.

In one embodiment, the felt layer of the felt material according to the invention is manufactured entirely or partially from renewable raw materials. Fibers of such renewable raw materials are for example polysaccharide fibers, and in particular fibers made from starches, cellulose, or guar gum or peptin fibers, or fibers made from derivatives thereof. When fibers or fiber components made of renewable raw materials are employed, this makes it possible to produce the felt material according to the invention as biologically renewable or compostable material.

In yet another embodiment, the felt layer is produced entirely or partially from fibers that are made from biogenic raw materials. Biogenic raw materials are materials of vegetable and animal origin. Suitable biogenic raw materials are for example feather creatine and mil casein.

The felt layer of the felt material according to the invention can consist of single fibers or of a mixture of fibers. When a mixture of fibers is used, it is possible to process fibers which have different characteristics to obtain a felt. The fibers of the fiber mixture can in this case differ for example in the thickness of the fiber, or in the fiber density, or in the surface structure of the fiber. It is thus possible to use for example fibers having a surface structure which supports felting (matting), which is the case for example with animal fibers, or wool fibers with scales. The fibers can be equipped for this purpose with inward and outward bulges or other surface structures. When fiber mixtures are used, the different fibers are distributed in the fiber fabric evenly or unevenly before they are processed to obtain a felt.

In one variant, the fiber sheets are pre-needled before the actual connection is induced. If several felt layers are employed, they can be also needled with different strengths. Accordingly, the surface weight of the felt layers can be also identical or different. It is also possible to use needling with a different strength in a single area within one felt layer. Such a different strength within one surface can be achieved for example with a different density of the arrangement of the needles in a needle board, or when different needle boards are used.

In one embodiment, the fiber mixture is designed in such a way that it has a fiber content which is particularly well handled by the felt needles, and a second fiber content which supports a further processing of the felt. A similar second fiber material can be formed for example from fusible fibers, so that the felt can be deformed by thermal pressing, compacting, smoothing or structuring. It is further also possible for example to treat the second fiber content with a chemical component which can then be further processed during the subsequent manufacturing process, for instance with UV radiation, with thermal curing or with a chemical reaction.

Depending on the application, the felt layer according to the invention can have different density and weight per surface area ($m^2$), wherein felts having a hardness between the hardness of soft cotton and that of wood can be employed. Similarly, the absorber-containing layer can be provided with different absorber polymers depending on the field of application, for example in the form of pellets, granules or fibers, which also contribute to the different hardness and density of the felt material according to the invention. In another embodiment, several materials and/or functional materials are combined in one felt layer so that the felt layer is provided in the form of a composite layer.

In a further embodiment, the felt layer is made entirely or at least partially from hollow fibers or functional fibers. Such functional fibers are for example fibers which are provided with latent heat storage, such as for instance phase change material PCM which is sold under the trademark name of Micronal® by BASF, or they can be offered or contained in an encapsulated form including fragrances, active ingredients and dyes. Other potentially useful functional materials include also metal fibers, such as for example silver fibers or fibers containing silver ions, as well as fibers containing fusible plastic materials or fusible surface coatings. Depending on the field of application, suitable felt fibers can comprise also heat-resistant fibers such as for example carbon fibers, and high-strength fibers such as aramide fibers. In addition, it is also possible to use fibers which are provided with superabsorber polymers as functional fibers. The functional fibers can in this case be designed in such a way that the fibers will react selectively to temperature, moisture content, pH value, voltage or pressure so that a different conduct is displayed depending on these parameters. Similarly, the fibers can be also designed so that they will bind selectively to certain chemical substances, or selectively generate certain chemical substances. The fibers can be also provided with an antistatic design in an embodiment to provide a dust-resistant finish.

The felt layer of the felt material according to the invention is in yet another embodiment partially or entirely encased in moisture-conducting materials.

In this manner, a capillary effect is achieved which leads the moisture into or away from the absorber-containing layer. As an alternative, instead of using encasing, an additional material component is used in this embodiment which can be for example cellulose fibers, flakes, shaped bodies or a powder so that water or moisture is also conducted through the capillary effect from or into the absorber-containing layer. The additional material can be for example also a laminate.

Other suitable functional fibers are for example light-guiding or light-storing fibers, such as for example polymer optic fibers (POF).

In another variant, the fibers of the felt layers are provided with further substances such as dyes, fragrances or auxiliary substances. For auxiliary substances can be used for example materials which create a water repellent design of the surface, or materials making it possible to create flame retarding characteristics of the surface. Another auxiliary substance, which can be for example introduced onto the fibers of the felt layer or between the felt layers, is an odor-binding material or an odor-binding substance, such as for example metal salts of resinolic acid, amino acids or other odor binders. These binders can be employed for example in encapsulated form so that they are released by the material only gradually.

In one embodiment, the fragrances, dyes and/or active ingredients are applied subsequently to the felt material according to the invention. For example, the felt material can be subsequently provided with fragrances or dyes so that it can be individually customized in this manner. Suitable active ingredients are for example odor-binding substances, substances which have a microbiocidal or insect repellent effect. In one type of an active ingredient, the material can be provided with indicator substances which indicate when the ventilation insert comes into contact with substances which for example limit or destroy the functional capability. This indication can be achieved for example with a color change. It is also possible to add as an active ingredient substances which accelerate drying of the absorber, such as materials which remove moisture from the absorber, or substances which generate heat with the flow of kinetic energy or with a chemical reaction. It is also possible to design a heatable felt material in order to achieve accelerated drying of the absorber.

In another embodiment, the felt material according to the invention is provided with auxiliary substances which improve the application characteristics for respective applications. For example, in a variant of the felt material according to the invention, the felt material is covered with skincare substances or wound healing materials. Suitable skincare substances or wound healing materials are for example dexpanthenol, Hamamelis (witch-hazel), chamomile, antioxidants, light stabilizers, hyaluronic acid, insect repellents, antimicrobial substances, essential oils, moisturizers or perfumes. The above named additives are according to this invention added directly or in encapsulated form, or as component parts of the fibers or of the absorber polymer.

In another variant, the felt layer of the felt material according to the invention is provided with a multilayered structure, wherein the various layers can consist of different fibers or materials. So for example, a woven layer can be connected with another layer made of feltable material. Also the connection of a layer made of a plastic material with a feltable fiber layer can be employed in accordance with the invention. In one embodiment form, the felt layer contains admixtures of the filter material according to the invention.

Suitable examples of mixtures are for example the functional fibers already described above, such as for instance PCM, ceramic fibers, glass fibers, carbon fibers, absorber polymer fibers and/or metallic fibers. The various material characteristics and flexibilities of the materials can be adjusted with the admixture of a corresponding fiber material.

When the felt material according to the invention comprises a first felt layer which is built on the arranged absorber layer and a second felt layer, the first and the second felt layers are either designed from the same felt material or from different felt materials, for instance with different surface weights or different fiber densities. The texture of the felt layer in this case will depend on the relevant application area. For example, if it is useful to put on one side of the felt material a filter carbon fiber in order to achieve a filtering effect before air or liquids, which are not conducive to swelling, reach the absorber-containing layer.

In other areas, one or both of the felt layers can be for example oriented in such a way that it has characteristics inducing the formation of drops of water. In yet another variant, both felt layers are coated with fragrances, active ingredients or dyes which are not impacted by the air streaming through the layers and which do not contribute to swelling so that the fragrances and active ingredients or dyes remain when the fluid leaves the felt material, or so that the felt layer is treated or textured in such a way that a substance such as an odor carrier or a salt is filtered out when it is passing through the layer.

Absorber-Containing Layer

The absorber-containing layer contains at least one absorber, and preferably an absorber which is attached to a carrier material. It is preferred when the absorber-containing layer of the felt material according to the invention is an absorber nonwoven fabric (nonwoven fabric), in particular preferred is a nonwoven fabric with absorber polymers. When the absorber nonwoven fabric is used, it can be also preneedled. The absorber nonwoven fabric function is provided with an absorber on one side or on both sides, or an absorber is included therein. The absorber is in the case preferably a superabsorber polymer, i.e. a polymer which is capable of swelling when it comes into contact with a liquid, in particular with water, and which is preferably selected from the group consisting of polyacrylic acid, polyacrylic acid copolymers, crosslinked sodium polyacrylate, casein, egg white and thermostatic elastomer composites. It is particularly preferred when absorber nonwoven fabrics Luquafleece® are employed which are made by BASF. Another suitable nonwoven fabric which is provided with superabsorber polymers is offered under the name Oasis® by the Technical Absorbents Company. As absorber polymers can be used for example superabsorbers such as HySorb® which are made by BASF AG, or Favor® which is made by Degussa AG. The absorber can be optionally also mixed with a filler so that the absorber and the filler form together an absorber-containing layer. Similarly, for example an absorber polymer-containing surface can be also used for absorber-containing surfaces, for example absorber polymer-containing surfaces such those that are used in the hygiene industry.

In yet another preferred embodiment, the absorber is placed in an AirLaid material. The AirLaid material in this case functions in the felt material as a filler. AirLaid materials are materials which are produced from cellulose and/or synthetic staple fibers using compressed air. Hence the name "AirLaid". A technique for the manufacturing of AirLaid materials is described for example in U.S. Pat. No. 4,640,810. The AirLaid materials used according to the invention can consist of several layers which are placed on top of each other, wherein the absorber can be arranged between several layers, or in the layers, i.e. mixed with the fibers. The layers are then compacted and for example thermally connected to each other.

Tissue materials or tissue-like materials are also suitable for filler material. A tissue material thus consists entirely or mainly of cellulose fibers and it is provided with a certain amount of pleating or creping. Known tissue materials are for example paper towels, tissue paper, or absorbent pads. In contrast to tissue materials, under tissue-like materials are understood materials which can be manufactured with modifications performed during a dry process, which includes wet crepe (Hygiene Crepe) and cellulose fiber. Tissue paper is characterized by an average grammage in the range of 15-30 g/m$^2$ (gsm), but it can also have lower values, as low as 5 g/m$^2$.

In an alternative embodiment, the absorber-containing layer contains as a carrier material fibers or material layers such as for example films which can be dissolved in aqueous or non-aqueous media, wherein the absorber is connected to the carrier material. This temporary absorber-containing layer is also inserted between the felt layers; however, the fibers of the absorber-containing layer are dissolved after the needling so that only the absorber which is not bound anymore to the absorber will remain between the felt layers without the carrier materials. The carrier material in the form of soluble substances or soluble fibers can be removed for example by washing it out or with compressed air, with heat, or chemically. Permeable spaces are created by the removal of the carrier material which results in improved permeability to air. Depending on the degree of the compaction of the felt material, the absorber is surrounded by the connecting fibers and more or less fixed by the insoluble components of the carrier material.

The selection of the absorber depends on which fluid is expected to cause the swelling of the absorber. When water is used for the swelling, it is preferred when the named superabsorbers are employed. In one embodiment, it is also possible to combine two or more absorber materials together so that an absorber responds to water and another absorber material responds to another fluid.

The shaping of the absorber polymer is preferably adjusted with respect to the size to ensure that the absorber polymer particles or fibers will substantially remain arranged between the felt layers during the matting and/or connecting fibers and that they are not rearranged together with the fibers.

For a filler can be used for example polymer compounds, thermoplastic-elastomer composites, animal fibers such as hair, feathers, leather, bone, vegetable fibers such as cotton, cellulose, cardboard, cloth, coconut shells, wood, fibers made of herbs, metallic fibers, mineral fibers, carbon fibers, wefts, rubber, or materials consisting of mixtures thereof. Powder or granules or materials having heat retaining properties such as for example micro-encapsulated paraffin waxes (PCM) can be also used. Alternatively, the filler can be also designed as a shaped body, for example in the form of capsules. The filling material is used for example to reduce the weight. If a liquid or water conducting filling material is employed, this material can also conduct the fluid or water that was already absorbed in the absorber with the formation of a specific moisture bridge outside, which can contribute to a faster evaporation of the water. The filling material and the amount of the filling material are selected in such a way that the swelling of the absorber and the closing of the felt material caused in this manner are adjusted depending on the application area. If the filling material is used to form a specific moisture bridge, it is advantageous when the evaporation surfaces are in contact with the object to be ventilated. Such evaporation surfaces can be for example upper materials of an article of clothing or of shoes. The application of such a filling material is in particular advantageous when the upper material itself cannot form any moisture bridge to the inner material and thus it can provide only a small evaporation surface. The absorber-containing layer can in one embodiment also include admixtures of other functional substances, such as for example activated carbon, silver ions or fragrances.

In another variant, the absorber-containing layer is made at least partially from superabsorber polymer fibers.

The absorber-containing layer is in another embodiment a swellable film, for example a plastic film made of thermoplastic polyurethane elastomer into which superabsorber polymers are mixed. When this film is employed, the felting of the fibers is performed in the first felt layer and in the second felt layer through the film, so that perforations are created in the film through which air can penetrate. If the felt layers additionally also contain superabsorber polymer fibers in another variant, the perforations can be closed with the swelling superabsorber polymer fibers. It is also known that the film can swell at a reduced speed, so that the diameter of the perforations can be reduced and the closing can be supported during contact with water.

In another embodiment, the absorber-containing layer is made partially or entirely from renewable raw materials. The carrier material on which are arranged for example the absorber polymers, thus consists of biodegradable fibers, such as for example polysaccharide fibers, in particular starch, cellulose, guaran, guar or peptin fibers. When the felt material according to the invention is provided with an absorber-containing layer consisting of renewable raw materials which are biodegradable raw materials and the felt layers at the same time also consist of biodegradable material, the entire felt material according to the invention is compostable.

Depending on the absorber-containing layer which is used, the expansion of the fluids can be adjusted within the surface of the felt material according to this invention. The expansion will in this case depend for example on the type and size of the particle, on the carrier material and the crosslinking of the absorber, for example a superabsorber polymer. The saturation of the felt material will be influenced in addition to the selection of the absorber material also by the barriers in the material. One barrier can be determined for example with stronger mechanical fixing, or with the type of the carrier material or of the felt layer which determines the texture of the absorber. It is also conceivable that the corresponding surfaces can be compressed in such a way that an expansion of a feltable substance is reduced or limited in a targeted manner.

The fluid is expanding when blocking of the gel does not occur from within of the absorber-containing layer. The absorber polymers swell so much that no full-surface moisture transport is possible. When fluid transport is desired, hydrophilic materials are added within the felt material according to the invention or connected with a felt layer. Hydrophilic materials can be provided for example as structural components of the carrier material of the absorber, or as a coating of the reactive material, or as an admixture which can be added as structural components of the transport surfaces, for example as fibers. Currently, for example cellulose fibers or particles are used in order to solve this problem. As an alternative, felt fibers are used which assume the transport function. When required, the transport materials of the felt are formed with a flat design in such a way that they do not penetrate through the felt surface but instead are projecting only into the absorber-containing layer and thus form the top and bottom side. A more uniform moisture transport can be provided in this manner. The moisture transport can be alternatively also achieved with a separate material which is connected with the felt material. The fluid transport can in another embodiment be realized with structures on the surface of the felt material which can also penetrate into the felt material. The structured surfaces then also serve as conduits which distribute initially the fluid through the material with a larger amount of fluid, although this fluid is then absorbed by the absorber more slowly. This will also circumvent the disadvantage created by the gel blocking.

Structure of the Felt Material According to the Invention

The felt material according to the invention is constructed from at least one felt layer, and at least partially from an absorber-containing layer, wherein the layers are needled together.

In a preferred embodiment, the felt material comprises at least three layers:
- a first felt layer,
- an absorber-containing layer, which is arranged at least partially on the first felt layer and which can comprise for example an absorber polymer fixed on the carrier material, and
- a second felt layer which is arranged on the other side of the absorber-containing layer for the first felt layer.

As long as the felt material according to the invention contains at least one first layer and at least one absorber-containing layer arranged on the first layer in partial areas, any combinations and any number of layers and felt layers can be manufactured. The number of the layers that are used depends on the desired material properties and on the planned application field. Common structures use for example three layers. They can consist of the first felt layer, an absorber-containing layer and a second layer, four layers including a first felt layer and absorber containing layer, a second felt layer and a covering layer, and five layers including a first layer, a first absorber-containing layer, a second felt layer and a covering layer, and five layers including a first felt layer, a first absorber-containing layer, a second felt layer, a second absorber-containing layer and a third felt layer. It is for example also possible to use two felt materials according to the invention with different layer superstructures or material properties which are combined in the felt construction with another, third felt layer mutually entangled with each other, or to use two felt layers felted over each other.

The strength of the connection between the first felt layer, the absorber-containing layer and/or the second layer is adjusted with the penetration depth of the fibers. A suitable penetration depth is selected depending on whether the first and the second felt layer should be mechanically connected with each other, or whether a connection is desired only through the absorber-containing layer placed in between.

The first and the second felt layer with the absorber-containing layer placed in between them are in this case mutually entangled in such a way that the different materials are not mutually penetrating each other, or that penetration of the materials is achieved at least partially or on the entire surface of both felt layers.

In one embodiment, the first and the second felt layer are mutually entangled in such a way that there is no direct mechanical connection or only a very limited direct mechanical connection between the first and the second felt layer and the top and the bottom side are thus created. Both layers are then connected to each other only through the absorber-containing layer which is arranged between the felt layers.

This embodiment is in particular employed when the top and the bottom side of the felt material according to the invention have different properties. It is for example possible to create a hydrophilic top side so that this side then conducts the mediums to the core function, namely to the absorber-containing layer. In contrast to that, the bottom side can be equipped with hydrophobic properties so that the medium is not conducted further to the carrier, for example an article of clothing. It is also possible to use reverse the order wherein the bottom side is created with a hydrophilic design and the top side is hydrophobic in another possible embodiment. As an alternative, it is also possible to use for example hydrophobic fibers on the top side of the felt and on the bottom side of the felt so that water can penetrate through the intermediate spaces between the fibers and so that it is thus always conducted to the absorber-containing layer and the water vapor can be absorbed at a distance from the absorber polymer. The felt material according to the invention is constructed for example so that one side of the felt is made of wool or silk, the core is made of a superabsorber polymer and the bottom side is made of polyester fibers.

Depending on the particular application area, the absorber-containing layer is arranged in partial regions of the felt material so that the felt material is provided with different properties in different regions. In this case, the absorber-containing layer is not felted with the super-absorber polymer on the entire surface but only in partial regions, for example so that it is incorporated in arrangements creating strips or grids. This means that that the parts in which there is no absorber-containing layer are more flexible in the wet state so that they can be used for example as designated creasing locations, or so that they can flexibly employed in regions in which an increased flexibility is required. Alternatively, the absorber-containing layer is arranged in the entire felt material, wherein it can have an equal or different density.

In one embodiment, the first felt layer forms on one side at the same time also the carrier material for the absorber polymer, for example so that the felt layer is provided with the absorber polymer only in one half of the cross section and so that it is formed from fiber materials which are free of absorbing material in the other half. The felt material according to the invention is obtained in this variant by covering the felt layer so that the absorber-containing layer will be located in the center with subsequent compacting (felting) of the three layers.

Such a material can be formed for example by applying absorber polymers to a carrier material. The superabsorber can be applied in this variant to fiber layers having any thicknesses or to felt layers, wherein the superabsorber is advantageously provided only on one side.

If the first felt layer and the second layer and the absorber-containing layer are arranged in the form of absorbers on a carrier material in such a way that the absorber-containing layer is located in the center, both felt layers will be grasped with the felt needles during the subsequent needling of the fibers and drawn through the felt structure. The absorber polymers, which have the form of lumpy granules and which are in any case not present as fibers, will not be grasped by the felt needles so that the absorber-containing layer is substantially enclosed by the felt layers after the end of the felt processing treatment.

In one variant, the first felt layer is at the same the carrier material for the absorber and the absorber is then a structural component of the felt layer, or it is connected with the felt layer or arranged on it.

In another variant, the felt material according to the invention is constructed of at least two layers:
- A first felt layer and
- an absorber-containing layer arranged at least in partial areas on the first felt layer.

The first felt layer is in this embodiment felted on one side on the absorber-containing layer, which is constructed for example from an absorber material fixed on a carrier material. This embodiment has the advantage that only one felt layer must be processed during the processing of the felt with needles on the absorber-containing layer, which results in mechanical stabilization of the absorber-containing layer. The absorber polymers contained in the absorber layer, for example superabsorber polymer particles, are reliably shielded from the felt layer either partially or preferably on the entire surface. The absorber polymers are then limited in their expansion both by the connecting fibers and also by the carrier material of the absorber-containing layer, or by the felt layer arranged above it. To what extent the individual components contribute to the limiting of the absorber depends on the particular embodiment. In one variant, the felt layer is arranged under the absorber-containing layer and a film or a laminate is arranged above the absorber-containing layer. The limiting of the swelling will then take place in one direction through the top surface cover or through the laminate. Accordingly, the felt layer contains uniform or different types of fibers, including also within the textile sheet. These types of fibers differ for example in their densities ($g/m^2$) and in their functions. For example, it is possible to apply excessive felting treatment so that the functional fibers deployed next to each other are partially or entirely overfelted.

In another embodiment, the absorber-containing layer does not contain any absorber prior to felting and instead it consists of an ordinary material. However, at least one of both layers, either the first or the second felt layer or both felt layers, contain superabsorber polymer fibers so that the superabsorber polymer fibers are drawn between both felt layers during the felt processing operation. In this case it is preferred when both felt fibers are made from a non-quelling material and when they form a hard and rigid felt. The superabsorber polymer fibers are in this case limited by the hard material of the felt in their expansion. Optionally, the felt material is not permeable to air directly after the manufacturing, wherein a displacement of the felt fibers occurs with the first swelling of the superabsorber polymer fibers. Cavities are then created during the shrinking of the absorber polymer fibers through which air can flow. The felt material must be in this case activated with the first washing to achieve the full functional capability.

In another embodiment, the felt material according to the invention is designed in such a way that that intermediate gaps or small cavities are arranged between the felt layers in which a strongly swelling absorber has ample space to absorb large amounts of fluids and to increase the permeability to air during the dry state. The intermediate gaps also improve the capability to introduce subsequently active ingredients, fragrances or dyes into the material, for example in the intermediate gaps. The intermediate gaps can be achieved for example with the felting treatment of a soluble material described above. This soluble material serves as a place holder so that the intermediate gaps described above are created after the material has been washed out or dissolved.

In another variant, the cavities are created in the felt with shaped parts such as for example parts shaped from plastic material. In this case, matting or felting takes places only in partial areas so that the felt material according to the invention is provided with a different felt structure over the entire surface. The shaped parts are used in this manner, for example in the form of a fiber-shaped part which was processed with the felting treatment in advance to create a network or to increase the stability, or to manufacture structural parts which have predetermined contours. Moreover, the shaped parts can be used to create cavities which are filled in with the absorber or with absorber granulate and possibly in addition also contribute to a compression of the connecting fibers during the swelling of the absorber.

In another variant, metallic or moldable fibers and strips are added to the felt material according to the invention either between the layers, or as a part of the absorber-containing layer, or as a part of one of the felt layer. A felt material constructed in this manner can be used for example for applications in which projecting evaporation surfaces are provided. These evaporation surfaces can then be bent so that an optimal fluid absorption or output is enabled.

One embodiment of the felt material according to the invention is designed in such a way that the surface of the felt material is provided with a structure. The structure is created for example by applying pressing or cutting or another felting process to the material. In another variant, the surface structure is produced by a surface layer. A structured surface can be used to produce areas which have different absorption capability for the liquid, as well as different delivery capability for the absorbed liquid. It is preferred when the surface structure is created with a rib structure which results in an enlarged surface. The structuring of the surface of the felt material according to the invention has the advantage that the impacted fluid is slowed down with a high flow rate so that it can be better conducted to the inner part of the felt material and to the absorber.

The elevations on the surface of the felt material lead in this case to mechanical turbulences and they slow down the flow of the water similarly to a breakwater. The air turbulences created by the elevations also lead to a faster evaporation of the fluid and thus to faster drying. The elevations of the surface structure can also serve as spacers and thus they can be provided for example with coating that does not absorb moisture, or with a waterproof coating, or treated with a surface treatment. The depressions obtained in the structured surface, which can have for example rib-shaped or strip-shaped form, can thus serve as conduits for fluid distribution and lead to a faster distribution of the liquid on the surface. The surface structure of the felt material according to the invention can thus be arranged on the respective object so that the wall or the covering layer of the object closes the remaining open side of the felt material and creates at least in partial areas a conduit that is closed on all sides. Furthermore, several felt material layers can be arranged one above the other so that these conduit structures can be formed for example with a semi-circular or with a circular design.

In another embodiment, the felt material according to the invention is provided with surface structures, tunnel structures or recesses which serve to increase the evaporation surface of the felt material according to the invention. The structures are in this case built on the surface or in the felt material, or they can be even built both on the surface and inside of it. The inner structures can be obtained for example with introduced component parts such as corrugated cardboard or elements made from plastic material. The inner structures have in another variant for example a wavy shape. By applying a first and a second felt layer onto both sides of the wave, a structure of the felt material according to the invention is created which is similar to corrugated cardboard, wherein the absorber polymers can be arranged for example in the valleys of the wave-shaped path, which is in this case the absorber-containing layer.

The felt material according to the invention is equipped in another embodiment with creasing points or breaking or separation points. The designated creasing and breaking points can be incorporated for example in the form of cuts, openings, pre-punched locations, perforations, precut grooves, scratches, or with pressing, melting or abrasion operations applied to the material. When heat or ultrasound is used, the incorporation of the designated creasing and designated breaking points is used to ensure that the corresponding openings will be sealed and swelling of the absorber polymer particles will be prevented. These embodiments make it possible for the user to adapt the felt material according to the invention to an application size, for example with a sealing material, without requiring that the edges be subsequently sealed.

The felt material according to the invention can be also pretreated if necessary, wherein it is activated by water, water vapor, humidity or a fluid. The permeability to air and the functionality can be improved in this manner for individual application fields since the felt material is in this case "pre-activated". Under pre-activation is understood relaxation of the fibers which is caused by the swelling of the absorber.

In another embodiment, the felt material according to the invention is coated on one or both outer sides with a material which is permeable to air and to water. The felt material is then optionally provided with perforations or openings in the layer which are permeable to air and water, preferably on the top site and/or the bottom side. These perforations or openings are selectively arranged on the top side and on the bottom side in the same locations, or they are mutually staggered. The perforations and the openings are in this case either designed in such a way that they penetrate only one part of the thickness or of the height of the felt layer but not up to the absorber-containing layer, or with perforations/openings which are smaller or only slightly larger than the absorber and which reach up to the absorber-containing layer. The openings on the top side and on the bottom side are preferably not formed as openings penetrating through the felt. It is preferred when the perforations or openings penetrate the felt layer in such a way that one absorber-containing layer and/or fibers protecting layer will still remain as a cover. The realization of the felt material which contains perforations or openings provides penetration protection wherein the felt material has a climate regulating effect. However, the penetration protection should be at the same time also used as protection for penetration of other gases and fluids. The perforations and openings can be formed for example by lasers, by burning, or using hot needles, needles, mechanical removal, chemical removal, air or water jet cutting, scratching, irradiation and treatment with a gas that allows controlled decomposition. In addition, the perforations or openings can be also created with dissolution of structural parts of the felt layer which serve as placeholders, as long as these placeholders can be dissolved and washed out with water or a suitable solvent or removed mechanically.

In another embodiment, the felt material according to the invention is provided with ruptures which penetrate the felt material partially or fully in its cross-section. These ruptures are partially or completely covered by oversprays or by a laminate. The laminate or the overspray is preferably provided with perforation so that water vapor can escape from the felt material according to the invention. The covered ruptures, i.e. the recesses, lead to ventilation during the movement of the felt. By changing the volume of the ruptures or of the recesses, air circulation occurs in the recesses during movements of the felt material. The air can then be transported through the openings from the oversprays or from the laminate, so that a cooling or ventilating effect is created when warmer air is displaced during drying. The openings or perforations in the laminate are thus either arranged in the area of the ruptures or recesses, or in the vicinity thereof. Depending on the form of the recesses or ruptures, the felt material according to the invention is provided with these recesses on one side or on both sides. When the oversprays or the laminate are attached at the height of the recesses or the ruptures, this blocks or changes the distance for the water transport between the opening and the felt, so that saturation occurs and the resulting closing effect, which is to say the barrier function, is blocked or delayed.

In another embodiment, the felt material according to the invention is also provided with recesses, ruptures or other structures, wherein the laminate or the oversprays follow these structures. When the openings are located in the perforations of the laminate or the oversprays are used in which recesses are provided, this makes it possible to prevent water from coming into direct contact with openings in the recesses. In this case, although the water would drip off from the surface, the moisture would still essentially be absorbed and released through the openings or perforations. The application of a laminate, the introduction of perforations or openings and the structuring is performed for example in a single operation. For example, pressing is ideally combined with heat, so that the laminate is connected with the felt material and the structures are formed at the same time and the opening or the perforations are created. As an alternative, the laminate is extended over the recesses and it is provided with openings or perforations.

The felt material according to the invention is in another embodiment provided with planar structures, or with lamellar or scale-shaped incisions. These structural elements are designed such that they change during absorption or delivery of water and/or a fluid. Therefore, the elements are raised or lowered from the surface of the felt material according to the invention. Accordingly, the surface modifications are used for example as design elements to make it possible to insert a logo or lettering. In addition, it is also possible to employ these design elements as an indicator or to use them to modify climate controlled properties, for example of the evaporation surfaces. As long as the structural elements are designed as text or as a pattern, it is possible to create a design which makes visible the presence or absence of the pattern of the balancing status of the felt material according to the invention.

The felt material according to the invention further also has the advantage that also other functional materials than absorber polymers are better bound in the felt material than conventional materials. For example PCMs are more strongly integrated into the material and they will therefore remain longer in the felt material according to the invention than usual materials which are coated with PCM.

Felt Material as a Structural Component

In another embodiment, the felt material is designed as a merchandize that is sold by the meter, or as sheet product and it is used in this form, for example as an insulating mat, or packaged for respective applications as a structural component. The felt material is in another embodiment manufactured directly so that it is provided with the form which is required for the application. In one embodiment form, the structural component according to the invention is for example manufactured also as a three-dimensional shaped body.

In the embodiment of the felt material in which it is used as a structural component, it is preferred when a metered or sheet product is obtained which is cut according to the application with a form which is created by pressing, for example with heat and pressure, or with form stamping or with lasers. The open edges, which remain after cutting and from which the absorber could leak, can be optionally closed before application, for example with seams, using stitching with the application of a material which is free-flowing at the time when the material is processed. The closing of the open cut edges with the processing of a flowing material can be performed for example with gluing or bonding techniques, such as with the hot melt procedure. The closing of the open cut edges with such an edge seal enables the application of a felt material in any form for various types of applications. With a large density of the connecting fibers, the edge seal may not be necessary. Alternatively, blanks which fit exactly into the opening which needs to be closed or a form-fitted bracket or frame can be also used. Overflowing of the absorber into the edge regions can be also prevented with flush abutting or folding of the felt material to the adjacent surfaces.

The edge sealing can be optionally also carried out during the cutting process, for example with hot stamping or by cutting with a hot tool and sealing of the side edges. Likewise, fusion with laser can be performed on the side edges so that the edge sealing is achieved in this manner. Other methods for edge sealing can use oversprays for the open edges, quilting or felting of the edges, pressing of the edges or enveloping of the overlapping surfaces and fixing of these surfaces according to one of the methods named above. The edge sealing can be also carried out with overspraying or with high-frequency welding.

Treatment of the Felt Material

The felt material according to the invention is in another embodiment provided with treated surfaces, which are used for example as a covering layer or for a treated surface, wherein one or both surfaces of the felt layers are optionally treated. The surface treatment is used to control properties such as permeability to water, permeability to air, permeability to liquids, dust permeability and/or regulation of the speed with which the water or the water vapor is delivered and removed. By treating the surface, other properties of the felt material can be also influenced, such as the color, as well as the material properties such as fire resistance and optical properties. For example, with irradiation of a black dyed material with sunlight, more heat will be absorbed by the material, so that the fluid bound in the absorber will be faster evaporated due to the higher heat. Similarly, for example filter pigments can be added, which also leads to a modified delivery speed. The surface treatment further also allows with the compression of the structures or with the removal of the material to determine the degree of flexibility of the material and/or to determine the desired degree of flexibility. The surface can be further also treated with fragrances or active ingredients as was already described above, such as for example UV filters. In addition, a biocidal treatment of the surface also makes it possible to provide protections against vermin infestation or to provide protection against germs or mold growth. It is also possible to provide the surface with the lotus flower effect, i.e. to induce rejection of dirt or oil.

The surface treatment is preferably carried out by the application of films or layers made of metal, plastic material, ceramic/polymer mixture, woven textiles on nonwoven textiles, leather or customary air-permeable materials, or by using vapor deposition or ionizing with metal. These materials can be perforated in order to increase the permeability to air. When using a material which has perforations or recesses, these perforations or recesses can be created in the covering layer before or after the binding with the felt layer. It is preferred when these perforations or recesses are created so that the covering layer and optionally also parts of the felt layer are removed or shifted. This can be achieved for example with burning, or using laser, sandblasting, etching, drilling, needles, piercing, grinding, mechanical removal, sawing or loosening of the fibers in some locations.

The covering layer can be impacted for example with vapor deposition with metals such as for example silver, by the application of cured, dry active ingredients or a dye containing fluids, or by soaking or coating with a substance that was fluid at the point when the processing was conducted.

When soaking or coating is applied to the material, the substance will penetrate the felt layer completely or partially depending on the material and on the application. In another variant, the top layer is extended to the open cut edges so that the covering layer at the same time forms the edge seal, which can be performed in one operation.

In another embodiment, the felt material is designed so that it is reinforced or shaped at least in some areas. The reinforcement of the felt material according to the invention can be performed using heat and/or pressure, wherein certain parts of the fibers create a thermal connection in the felt layers. Alternatively, a reinforcement of the felt material can be carried out with soaking or depositing using a substance which is fluid at the point when processing is performed and which penetrates in partial areas into the felt material. A desired flexibility can be also created with partial impregnation with curable materials, so that a particular further processing of the felt material can be performed to create shaped parts. In another alternative, the reinforcements are introduced as a separate element, for example in the form of shaped parts made of plastic or metal. These parts can be integrated during the felting treatment into the felt material, or they can be introduced subsequently.

In another embodiment, the felt material according to the invention is provided with locking elements which are arranged horizontally or vertically, preferably vertically/horizontally, on the surface of the felt, for example parallel to the connecting fibers. The locking elements also contribute to limiting the expansion of the absorber. The locking elements contain for example a material which is fluid at the point when the processing is performed and which is applied for example by spraying on the felt material, such as a plastic material. Suitable locking elements are provided for example in the strip form, sheet form or in the form of a grid and they are also used to stabilize the felt material when it is used for applications requiring higher mechanical loads. Furthermore, the use of locking elements is suitable when the felt material according to the invention is used for inserts or for structural components because the locking elements can then be used as edge seals, or they can be provided with the form of the structural component. The locking elements also make it possible to define individual areas in order to prevent spreading of moisture or water on surfaces. This spreading can be limited to certain areas of the felt material, so that wet/moist and dry areas are formed.

In another alternative, permanently deformable fibers or materials or fusible fibers are used for the reinforcing of the felt material according to the invention, which allow deformation and fixing of the felt material with thermal pressing or curing by heat or with UV irradiation. Such materials can be for example thermosensitive reinforcements such as paraffin. The introduction of reinforcements into the felt material according to the invention is particularly relevant to technical applications such as medical applications of the felt material according to the invention. For example, when reinforcements are employed, such as customizable immobilizing medical splints, medical dressings, orthopedic inserts or technical insulation materials, an adjustment can be carried out on site. This also applies to fields of technical applications in which the material can be used for climatic control, for example for climatic control and pressure equalization in packaging for bulk materials such as cement bags or plastic bags for chemicals, or for climatic control of packaging materials such as for example containers.

The surface of the felt material according to the invention is in another variant directed with support brackets, which serve to prevent a moisture bridge or to prevent a planar contact area for example in a surface in which high heat or cold is developed, or to provide insulation against electricity.

The surface of the felt material according to the invention is in another variant provided with an insulation layer protecting against harmful media. Such an insulation layer can be a filter layer which filters out for example salts or other substances that could cause damage to the absorber or to the fibers of the felt material. The insulation layer is in this case preferably permeable to a fluid such as water and to air.

In order to prevent the formation of a moisture bridge to the surrounding material or to the carrier of the respective objects, it is preferred when a material which does not conduct water is used on the side facing the body, or when the material is equipped with corresponding properties.

The formation of a moisture bridge is additionally prevented with plastic components such as carrier layers, protective grids and distance surfaces. The prevention of a direct body contact with corresponding surfaces not only has the advantage that an air layer is formed, but in addition, the differences in cold of the temperature outside are not led directly further through the moist material of the absorber or other component parts of the ventilation insert to the carrier. The structures facing the body have the advantage that an air current can be circulated on the side of the body, and moreover, strong sweating does not cause tactile contact through water drops, so that for example perspiration will not cause the felt material according to the invention to become closed prematurely so that ventilation is then interrupted in this manner. For the material which is facing the body can be used for example materials that are pleasant to skin but that do not conduct water, or water conducting materials that are pleasant to skin can be also used. Such materials are for example micro-fibers or membranes which are provided in some areas in which the absorber is located with air-permeable openings so that an air-permeable layer is formed in this manner. When such materials are utilized, the advantage of permeability to water can be combined with the improved air permeability of the felt material according to this invention.

In another embodiment, the felt material according to the invention contains at least one of the felt layers and/or the absorber-containing layer, or additional materials are contained as an additional layer which are suitable for absorption of targeted substances, or which are compatible with certain environmental conditions. If the materials are released, materials suitable for application are materials which allow releasing of functional substances depending on the following parameters:

- the pH value
- temperature
- salinity
- the type of the fluid or gas
- chemical substances
- enzymes
- pressure
- mechanical influences
- chemical influences
- drying period
- wetting time and/or
- frequency
- current/voltage
- irradiation, for example UV, IR.

Further, it is also preferred when materials are used which allow releasing of functional substances under the influence of microorganisms, fungi, algae or vegetation.

For example, the felt material according to the invention can be provided with a material which acts as an indicator, wherein for this indicator to become activated, the surface must first come into contact with water or with water vapor. The coloring of the indicator in this case reveals for example the degree of saturation, or the time still remaining for the function after a contact with harmful substances. It is also conceivable that several such reactions of a functional substance can be combined with each other or connected in series.

The felt material can be also designed in such a way that it can be washed or cleaned with chemical cleaning. Mechanical strength can be used to remove dust or dirt mechanically from the felt material, for example with striking, blowing or vacuuming.

It is preferred when the felt material according to the invention is machine washable. The machine-washable felt material is in this case usually designed so that the edges of the felt material are sealed in order to prevent partial leaking of the absorber. When the edges of the felt material according to the invention are not sealed, the absorber will leak out during washing in a washing machine in lateral areas in very small quantities. The major portion of the absorber polymer particles is maintained by the perpendicularly arranged felt fibers between the felt layers in the material. Planar leaking of the absorber polymer was therefore not observed in the wet state or during washing. The washability of the felt material according to the invention thus represents a significant advantage over absorber-containing materials known from prior art which are not all washable, and in particular not machine washable.

It was further also observed that swelling of the absorber polymer occurs during washing or during washing with a washing machine, which at leads to at least partial loosening of the felt because the fibers are partially shifted depending on the texturing of the fiber and on the degree of needling of the felt. In addition, the machine washing causes in some embodiments of the felt material according to the invention additional felting, in particular in the outer layers, wherein additional and reinforced incorporation of the absorber polymer takes place between the layer and escaping of the absorber polymer is prevented.

Manufacturing of the Felt Material

According to the invention, the manufacturing of the felt material is performed with needle felting, wherein the material is mechanically penetrated with numerous needles which have barbs. With the repeated insertion, the fibers of different layers are mutually intertwined so that a felt or needled nonwoven fabric substance is obtained. The fiber material is compressed with the needle felting so that a uniform flat structure of the textile is formed.

Alternatively, the felt material can be compressed further. Further compression is achieved with heat and/or by soaking the felt material in substances that are fluid at the point of processing. The method for manufacturing the felt material according to the invention is realized so that the fibers of one of felt layers penetrate at least the absorber-containing layer, and preferably also another felt layer. The fibers of the first layer primarily penetrate the second layer. It is also possible that the same penetration ratio is created for all fiber layers, while different penetration ratios can be achieved for different fiber layers.

The layers from which the connecting fiber content originates are therefore optionally matched in their material texture and the amount of the fibers to the desired material. According to the invention, materials wherein the penetration of the connecting fibers of the first felt layer is carried out through the second felt layer are also manufactured, so that the penetration of the second felt layer is carried out through the first layer, or so that the penetration of the first and of the second layer is carried out through the carrier material of the absorber-containing layer or through the absorber-containing layer.

A felt material containing a superabsorber felt material can be manufactured with cold felting as a metered product and optionally customized in further processing operations, connected with molded parts or otherwise improved (lotus effect, silver ions).

The manufacturing of the felt material according to the invention is performed in one embodiment so that the felt is felted to a size that corresponding to the end application. This is possible because the felt material according to the invention can be manufactured also with felts which have a small surface.

According to the invention it is optimal when the felt material is filled in any locations during the manufacturing of the felt material. It is for example possible to fill in the functional material only at the side edges.

The felt material according to the invention which can be contained as functional material includes for example shape memory materials which can be activated by temperature differences or other triggers such as UV radiation, heat, cold, moisture, current or voltage. These functional materials can cause shape memory reactions and thus adjust the texture of the felt and contribute in this manner to another type of mechanical fixing or to connections available with other fibers of non-activated shape memory materials. The shape memory materials are in one embodiment a part of the surface treatment and they support for example additional closing or opening mechanisms on the surface.

It is also possible to use shape memory materials for example as an indicator of wetting or of the loading status of the absorber.

In one embodiment of the method according to the invention, the felt material is manufactured such that it contains designated creasing locations and breaking points. The designated creasing locations and breaking points can be produced with different methods, such as for example with cutting, by creating incisions, or with the introduction of substances, perforation, punching, piercing, removal of material, pressing, fusing, pre-perforating, through-perforating, laser cutting, chemical stripping, chemical treatment, with an irradiating or compacting treatment or with treatments using corresponding laminates or coatings.

In one embodiment of the method according to the invention, the manufacturing of the felt material according to the invention is performed with needling which is followed by additional wet felting. This makes the surface of the felt material additionally compacted and deformation of the felt can be achieved with the wet felting also in conjunction with alkalis or dilute acids. The process is in this case realized in a variant wherein some areas are felted with needle felting and other areas are felted with wet felting. Both felting techniques can be in this embodiment mutually combined with any felt material.

The properties of the felt material according to the invention can be influenced during the manufacturing of the felt material according to the invention depending on the strength, duration, arrangement, amount, density and functionality of the needles. For example, a different length of the needles results in a different penetration and thus also in bonding with a different strength of the connecting fibers between the layers.

Optionally, needles can be arranged on a needle bed of the felt machine with needles having different barbs, different diameters, different lengths and/or different forms.

Optionally, an auxiliary means is used during the felting process which exerts an influence on the mechanical strength of the felt. The usual auxiliary means which are used for felting are in this case applied over the entire width of the felt or only in some areas.

In another embodiment of the method according to the invention, at least partially hollow needles are employed so that targeted substances can be filled in the materials with hollow needles. It is preferred when substances which are introduced lead to a targeted influencing of the felt properties. It is thus possible to use for instance gases which cause targeted roughening of the fibers. It is for example also possible to introduce in this manner materials which induce shape memory reactions as a result of differences in temperature or other precipitating factors such as heat, cold, steam or UV irradiation. This can be also used to adjust the texturing of the felt materials because the areas in which the activated functional fibers are introduced will display other mechanical strengthening and another connection between the fibers then areas with non-activated materials.

During the felting process according to the invention, the felt needles are in one embodiment heated or cooled. Heating of the needles is particularly preferred when parts of the material to be felted or overfelted consist of fusible fibers. A better connection is then created between the fibers with the non-heated fibers with the heat generated by felting needles. Alternatively, the material to be felted or overfelted can be heated and then cooled in some areas with cooled needles so that different fiber connection strengths and material properties can be achieved.

In another optional process step, the density of the fiber floor can be enhanced during the felting process additionally to the felting with needles by using heat or pressure after the felting.

With felt materials which are in addition to a covering layer also equipped with a laminate layer, the covering layer or the laminate are in one variant fixed and attached to one of the felt layers. The processing step in which the laminate is attached during felting and the subsequent full felting can be carried out in sequential processing steps which follow immediately one after another. It is also possible to interrupt one felting operation that has already started then to apply the laminate or the covering layer and continue the felting operation with this layer.

During the manufacture of the felt material according to the invention, the layers are heated or cooled just before the mechanical consolidation in order to achieve a better connection or to create connection area which have different properties. When the various layers are joined together as sheets just before the felting, it is also conceivable that the individual sheets can be joined together using different temperature, or so that all the sheets are heated or cooled to the same temperature. In addition, it is also possible to set different temperature regions within the felt material during the felting operation since temperatures depend on the frequency of needle felting which is based on the form and the structure of the needles.

In another embodiment of the method according to the invention, a precursor of the absorber polymer is introduced into the absorber-containing layer. The actual polymerization to absorber polymer then occurs during the felting procedure or after the felting has been finished. If the method is realized by means of hollow needles, the absorber polymer or a precursor of the absorber polymer can be introduced into the material during the felting operation.

In another embodiment, the method according to the invention is carried out so that the swollen or partially swollen absorber polymers are inserted into the absorber-containing layer and then processed with overfelting. Defined intermediate gaps are thus created after drying of the absorber-containing layer with the felt material according to the invention. This enables a targeted adjustment of the maximum loading amounts which can be accommodated by the felt material according to this invention. When for example the felt material is capable of absorbing 2 $l/m^2$ of fluids, this amount is added to the absorber-containing layer which is then processed with felting. When low-stretch felt fibers are used, the maximum amount of the felt material that can be accommodated is thus defined in advance.

It has been shown that pre-swollen absorbent material is softer than the absorber material which has not been swollen and wetted yet. Accordingly, the pre-swollen or swollen absorber material is easier to process. This is probably due to the fact that many materials are more resilient and display a higher elasticity in the wet, soft state than dry and hard materials, so that the felting process is facilitated in this manner.

In another embodiment of the method according to the invention, the connecting fibers of the felt material are driven through a layer which does not contain fibers. Such a layer is for example a laminate or a layer made of plastic. In order to improve the mutual interlocking between the layers, fibers which are driven through a non-fibrous layer are folded over after the felting operation, for example by milling, rolling or pressing. When the fibers are fusible fibers, they can be compressed with heat or compression so that they will be fixed onto the layer which does not contain fibers. It is essentially also possible to design the layer which does not contain fibers in such a way that an adhesive design of this layer is created and the connecting fibers are glued to this layer or fixed on this layer during the folding. The layer which does not contain fibers can be constructed for example as a thermoplastic layer, or it can be equipped with an adhesive layer.

In a variant of the manufacturing method for producing the felt material according to the invention, the felt material is manufactured as a three-dimensional shaped body. This three-dimensional shaped body is produced with targeted felting of respective forms, by grinding, cutting or with the removal of a corresponding base body of the felt. Alternatively, the felt material according to the invention can be also manufactured as a hose.

Structural Component Made of the Felt Material

A subject of the invention is further also a structural component of the felt material according to the invention as described above.

The structural component is preferably obtained by cutting, sawing or punching it from the felt material as metered or sheet product as described above.

The structural component is then processed with the edge sealing method mentioned above to prevent leaking of the absorber at the open cut edges. In another embodiment, the structural component is provided on its edges with connecting elements which enable fitting of the structural component to an article of clothing, footwear or another application object. The connecting elements can be produced for example by overspraying with a plastic material, with a screw connection, adhesive connections, welded connections, clamp connections or with plug-in connections.

The embodiments of the structural component which has a connecting element are preferably formed as an extension of the felt layer. The connection elements are used to fix the structural component to the object or material that is to be ventilated, dried or sealed. The connection to the connecting element can be created for example with a magnetic connection, a click-in connection, plug-in connection, sliding connection, inverted connection, adhesive connection, or with folding connection, thermoplastic welding or stitching. The structural component is positioned by means of the connecting element over an opening in the textile to be ventilated or the object to be ventilated so that it completely covers this opening. In one embodiment, the connecting elements are designed in such a way that the structural element according to the invention is exchangeable. The structural component can in this case be constructed as a disposable article which can be replaced after it has been used once. Less preferred is a structural component which is designed as a non-reversible sealing surface.

In one embodiment, the connecting elements are designed so that the structural component can be replaced with a new structural component. A similar replacement can be also used to impart other properties to a structural component, for example to create additional functions for a ventilation insert which are thus imparted to the object to be ventilated. This embodiment is used for example in particular for safety helmets or for electrical articles.

In another embodiment, the connecting elements are provided with structures having bulges or indentations which, when they are matched with precision, make it possible to fix the structural component to the object to be ventilated. The connecting elements are for example additional structural components and the connection can be carried out for instance with extrusion coating with a plastic material, using gluing, screwing, riveting, or with a plug-in connection or with sewing. The connecting elements can be manufactured with different degrees of strength depending on the field of application. The surfaces of the elements are preferably thin and they meet outwardly at zero. It is preferred when the connecting elements can be textured already during the extrusion coating manufacturing stage or subsequently with mechanical roughening, etching, irradiation with UV light or with treatment with gases such as ozone. A suitably textured surface of the connection element facilitates the attachment to the object to be ventilated when a connection method such as gluing or welding or the like is selected.

The structural component can be similarly to the felt material according to the invention employed for many different fields of application in which supplying of air, ventilation or dehumidification is required on the one hand, while protection from water or other fluids is also desirable.

In another application, the structural component is designed without the edge sealing, but it is optionally provided with a frame which encloses the molded part of the felt so that it is flush at the side edges. The structural component is then inserted into the frame or the object to be ventilated so that the frame or the edges prevent the releasing of the absorber and so that they limit the scope of its extension. The structural component according to the invention is then customized such that it fits into the end product and so that it can be fixed therein.

In another embodiment, the structural component is designed in such a way that the plastic material is partially sprayed over, under or provided with the felt material according to the invention. The felt material according to the invention and the plastic material are thus either used to create a material connection in advance, or to form structural components which can be separated from each other. As far as the object which is provided with the felt material is concerned, the felt material according to the invention is in this case either fully or partially arranged on the outside or on the inside. For example, when it is used for handles of tools, the plastic handle is located inside the tool and enclosed outside by the felt material. With another design, the textile part is for example constructed as an inner shoe of a rubber boot and provided with a plastic material which is sprayed over it to form the rubber boot. A comparable combination of plastic material and felt material can be also used when the plastic material is sprayed on molded knee-protecting pads or safety helmets or shoe soles.

The use of the Felt Material According to the Invention and of the Structural Components According to the Invention The felt material and the structural components according to the invention can be used everywhere were climatic regulation is desired, such as for ventilation or dehumidification, which is to say when supplying of air is desired and when it is desirable that contact with fluids be prevented, or when targeting supplying of removal of water is desired. Accordingly, there are many possible applications for the felt material according to the invention, both for textile and for non-textile objects. Depending on the field of application, the felt material according to the invention serves as a structural part that is used for climatic regulation in the form of ventilation, wherein the barrier function which leads to the self-closing of the material protects from water or liquids. Due to the mechanical strength, the material can be in this case exposed to significantly higher loads than customary materials which contain an absorber. The material according to the invention can be also employed advantageously for sealing or surfaces or for dehumidification, or for a targeted removal of water or water vapors. The material according to the invention is thus in particular employed for climatic regulation through ventilation, for climatic regulation through dehumidification or humidification, and for automatic sealing of textile and non-textile objects.

One possible application of the felt according to the invention is when it is employed as upper shoe material which is permeable to air based on the properties of the felt and which is also waterproof as it is equipped with the absorber-containing layer. In order to use it as a shoe material, the felt material according to the invention is for example processed with punching to create the desired form, or further processed to seal the open cut edges, or processed with the application of a surface treatment. As an alternative, spraying can be applied over or to the felt material or the structural component, either partially or fully, for example to produce a rubber boot. An upper shoe material from the felt according to the invention or provided with the structural components according to the invention has the advantage that thanks to its air permeability, it also has a moisture regulating effect because water vapor is transported away from the inner part of the shoe.

Another possible use for the felt according to the invention is when it is used as an insert in a shoe sole or for inner shoe soles. As a component in the shoe sole, the felt according to the invention enables both ventilation of the feet as well as removal of moisture, such as bodily perspiration, from the shoe. When it comes into contact with moisture, for example through a puddle or when it rains, the shoe sole closes itself automatically. In another application, the inner sole or insertion sole is provided with absorbers, which means that the shock absorption of the felt according to the invention changes with the swelling of the absorber. The sole or the shoe is thus provided with damping characteristics which are different during wet conditions and during dry conditions.

Another use of the felt material according to the invention is represented by ventilation of articles of clothing. In this case, the felt material according to the invention is employed for example as lining material or as a part of the surface material of an article of clothing. Optionally, structural components made from the felt material according to the invention can be also placed in clothing and used for ventilation. This enables supply of air and ventilation while an article of clothing is worn, such as for example in jackets, pants, caps or vests. This makes it possible to increase the comfort level of the person wearing the clothing because moisture which is built up in an article of clothing is transported outside. At the same time, however, there is the risk that water or a fluid will penetrate into the inner part of the article of clothing because in these cases the felt material or the structural components according to the invention will be closed as soon as they come into contact with water.

In another embodiment, the felt material or the structural component made from a felt material according to the invention is incorporated into the clothing as a structural component/functional element which is not visible. A functional element obtained from the felt according to the invention is for example covered with a fabric layer or a layer of another functional material, such as for example a climatic membrane or other materials that are open to water and water vapor materials.

When the felt material according to the invention or its structural components are used for dehumidification of clothing, the material is used for example as an absorbent pad in the shoulder region of articles of clothing, such as jackets or sport jackets. The material according to the invention absorbs moisture and then gradually releases the moisture through evaporation into the environment. This makes it possible to prevent the feeling of uncomfortable wetness in some areas of the article of clothing. Thanks to the mechanical strength of the material according to the invention, the inserts can remain permanently in the clothing article, which was not possible with absorber-containing materials available until now, and it was not possible to integrate them into the lining of the article of clothing because they are not washable and with a high volume they are no longer "invisible" in the article of clothing.

The water or moisture absorption of the felt material or of the structural components according to the invention also makes it possible to use it as a dehumidification insert in areas in which condensation water is collected, such in tents, or in the packaging or housings of electronic devices. In these cases, the dehumidification insert absorbs the water that is trickling down and then releases it gradually into the environment. This enables climatic regulation in the tent or in the container. The use as a dehumidification insert is thus conceivable anywhere where large temperature differences exist. For example, the felt material according to the invention or structural parts thereof can be used in air conditioners, in refrigerators or as an insert in insulation media such as cooler bags. This is especially useful for targeted or accidental thawing when a large and excessive amount of condensation water is generated.

In another application of the felt material according to the invention, the felt material or structural components thereof can be used used for climatic regulation in special packaging or for technical applications. When the inner part of the packaging is very dry and when the moisture should not fall below a certain amount of moisture, such as for example during the transport of perishable products such as vegetables, the felt material or a structural component thereof can transport or deliver water vapor when the air is very dry into the interior of the packaging.

Another possible use is in various applications to floor coverings. First, the felt material according to the invention can be used in carpet flooring. The felt material is in this case used as a carrier or as a fixing layer for the fluorine fibers of the carpet flooring. The fluorine fibers are projected for example through the felt and they are in contact with the absorber-containing layer so that they are used for transporting water and moisture. A correspondingly equipped carpet flooring allows fast absorption of fluid which can be conducted in a targeted manner in the absorber-containing layer so that the carpet flooring can dry out faster and so that no pools of liquid will remain on the carpet. The moisture is then discharged from the absorber-containing layer slowly and in a uniform manner through evaporation. Moreover, the felt material according to the invention is also suitable for an intermediate layer and for footfall sound insulation in hard floor coverings such as boards, strip flooring or laminates. Larger amounts of fluids can thus be also absorbed in this manner and for example swelling of laminates or of strip flooring can be reduced or prevented. Such an application is appropriate in every case when the type of the floor covering is such that it protects the carpet flooring or the hard material from moisture and when the moisture should be conducted away in a targeted manner. In addition, such an application of the felt material in floor coverings helps to improve the climate in the room.

The felt material according to the invention can be also used in the construction field for intermediate sealing, for instance for walls or in the form of felt tiles even in the floor, ceiling or wall area. Moreover, it can be also used for roof tiles or as a structural component of roof coverings such as roof insulation sheets, or of green roof, insulation layers or roof sheets.

Another possible application in the construction field is using the material as a covering in the form of a base coating or a wall coating. Unlike with other open and capillary materials, the wall is thus effectively protected from rising dampness. Due to the mechanical controllability of the felt material according to the invention, the invention is highly suited for use as a wall covering.

The water absorption and water desorption of the felt material according to the invention is further also used for irrigation lines or for irrigation elements employed for plants.

Irrigation lines which are introduced into earth or in a vegetation substrate consist, partially or entirely, of the felt material according to the invention. The irrigation line from the material according to the invention will give only as much water from the interior to the soil or to the vegetation substance as can be absorbed thereby. Partial regions of the irrigation lines or irrigation elements in which there is no water are at the same time open to air so that ventilation of the soil or of the vegetation substrate takes place. In addition, it is also possible to introduce targeted growth promoting media or gases in the soil in the areas which are not filled with water. Ventilation of such plant systems in this manner is also possible when the substrate or the soil is covered with a foil to retain water and heat. The buildup of dampness, as well as drying out of soil can thus be prevented with the use of the irrigation lines or irrigation elements made of the material according to the invention. The irrigation elements can be also constructed for example as pots for plants or plant propagation elements.

In another application, the felt material according to the invention is employed as a collector of condensation water. For example, sheets made of the material according to the invention can be positioned horizontally, or preferably more or less upright to perpendicularly in order to absorb fog, dew or air humidity. It is preferred when the surfaces of the felt material according to the invention are structured for example with a scaly or with the strip shape having openings which are preferably oriented upwards in order to increase water absorption. With the structuring of the surface, it is easier to conduct the water into the absorber-containing layer of the material according to the invention. In one embodiment of a collector of condensation water, the felt material additionally also contains materials which can store heat or cold, such as for example PCM or paraffin. Lower temperatures at night allow condensation of the water vapor in the morning on the felt surface. The residual heat stored during the day is available to the plants also in the night. In addition, the felt material according to the invention is optionally coated so that the surface reflects infrared irradiation in order to prevent overheating of the surfaces during the day, which results in evaporation of the absorbed water. In another embodiment, the collector of condensation water is produced from the felt material according to the invention so that the surface of the felt is provided with structures or openings from which the plants grow, wherein these openings are created as small as possible to prevent loss and deviation of water. Optimally, the surfaces are produced from the felt material according to the invention in such a way that air or wind can flow uniformly around these surfaces and so that they are set up at a sufficient distance from the floor not to impede plant growth.

The collector of condensation water which is made from the felt material according to this invention and which is coated with PRM or paraffin can be used effectively in particular in coastal areas in the vicinity of lakes or other water surfaces, in forest or jungle areas, or near mountains. This is particularly evident in the morning hours when low temperatures of the felt surfaces according to the invention retain a high air humidity, fog or dew and the heat storing media store the cool of the night and thus keep the temperature of the felt surface according to the invention cool longer.

Furthermore, collectors of condensation water made of the felt surfaces according to the invention can be employed in greenhouse surfaces, and they can be used partially or entirely as a direct growth substrate or combined with such substrates.

The use of the felt material according to the invention or of structural parts thereof will now be further explained based on the following embodiments and examples:

When it is used in a surface, the structural component can be used for example as a part of a shin bone guard or of a safety helmet, or it can be a component thereof.

The felt material or the structural component can be used for ventilation or for climatic regulation of military protective equipment such as protective suits. For example, when it is used in protective suits of jet pilots which are subjected to high pressures, the material prevents penetration of water if the pilot had to eject himself from the ejection seat of the airplane.

When used in medical technology, the structural component can be employed in splints such as those that are used for broken bones, in particular in protective covers for injuries or for inflatable splints used for first aid with accidents. The healing process is accelerated with the improved circulation of air which also contributes to better comfort when the splints are worn. The components can be at the same time used both in veterinary medicine and in human medicine. In this embodiment, the structural component can be also provided with a dye that provides a visual indication as to how long the splint must be worn. In addition, hydrochromic dyes can be used which indicate when the dressing or the splint has come into contact with water and thus must be replaced.

The structural component can be also used in or for furniture surfaces, for example in chair or sitting surfaces of baby carriages, for infant carriers or car seats for babies, or as a covering for furniture or other upholstered objects. Ventilation is thus enabled while protection from wetness or moistures is provided at the same time. Similarly, it is also conceivable that the structural component can be used in washable mattress covers or as a casing of materials which do not absorb any moisture. For example, a casing for air mattresses or neck pads would improve the comfort during sweating when this object is used.

The structural component according to the invention can be used in the construction industry, for example for ventilation of buildings, for well fitting windows, or for improved insulation to prevent vapor barriers.

Other possible applications of the structural component according to the invention include covers, plastic sheeting and housings such as for cable harnesses, fuse boxes, or headlight boxes in which the structural component can prevent accumulation of condensation water. This prevention of condensation water can be also achieved when the structural component according to the invention is employed in equipment, cars, motorcycles, trailers, containers, cargo holds, poster holders, tents, sleeping bags, display boxes or greenhouses.

The structural component can be optionally also used for ventilation of special containers which are used for storage of substances containing liquids or substances sensitive to liquids such as building materials (cement, adhesives), fodder, foodstuffs or medical products.

The structural component can contain in addition to the absorber also active ingredients and it can be thus designed as a special filter, for example by using it in a protective helmet, a vacuum cleaner or a dust mask. When the absorber is combined in the structural component with activated charcoal, the active charcoal is effective against odors, while the structural component at the same time prevents leaking of fluids onto electronics.

The structural component can be arranged in an article of clothing, in a surface or in an object so that it serves as a special valve and as a barrier layer during emergency landing on water or as a fluid barrier. The structural component can be in this case coupled with electronic sensors, which for instance turn off electronic components or maintain a certain type of control when the structural component comes into contact with water or fluids.

The structural component can be designed such that it functions as a current regulator: in this embodiment, the covering layer is made of copper and the covering layer on the opposite side is made of another material such as zinc. When the absorber which is located between the covering layers becomes wet, electric current is created which can be used by a signal detector such as a light diode or another electronic component or which can be used to break a circuit. This can be employed for example in children's clothing or children's shoes which can flash or emit a tone if they become wet. Here, individual chambers of the structural component can be connected in series as batteries.

In order to demonstrate the felt material according to the invention, the felt material is integrated in a test device. The test device consist for example of a hollow body which is open on one side in which the structural component according to the invention is inserted. In the open state, it is possible to blow air through the structural component as one would blow air through an air whistle. When the component become wet, this exerts an effect on the test device so that air can no longer be blown through it.

The felt material according to the invention can be used as a filter, wherein the superabsorber polymer binds for example to water from fuel substances or to fiber content, so that this can be used for filtering of dust particles. Alternatively, the felt material according to the invention can be also used with another material which is suitable for filtering, such as for example activated charcoal, or with a fragrance or an active ingredient which facilitates filtering.

The felt material according to the invention can be used as a seal, for example as an O-ring seal or as a flat ring seal for valves, or it can be inserted as a washer. This has the advantage that existing seals which are provided only in the static state or react slowly to water can be simply replaced in the required sealing surfaces. The simplest version which is provided with an air permeable/pressure compensation seal is punched out with corresponding O-ring seals/surfaces from the felt material according to the invention. These sealing elements can be inserted between two surfaces such that the extension of the absorber is additionally limited within the felt structure in addition to the limit that is created by the connecting fibers. The pressure resistance (bar), the permeability to air and the reaction speed of the opening can be controlled depending on the amount of applied pressure. These characteristics are also influenced by the degree of felting. Depending on whether a very dense fiber structure is created for the product or whether instead a relatively loose fiber connection or even none at all exists, only a slight sealing of the swelling absorber is achieved.

The felt material is in addition also suitable to be used as a seal, for example as a ring seal, for windows or doors or for other application in the construction field.

When the felt material according to the invention is used as a seal, it can be also employed as a sealing medium. The felt material according to the invention is in this case inserted between two surfaces so that it fills the gap between them during the swelling and so that this gap is closed. For example elastic fibers can be used for this purpose, wherein the felt surfaces are pressed between the surfaces to be sealed, or a felt material is used which has a predefined volume increase.

The felt material according to the invention is in addition also used in various applications in the packaging industry. For example, it is used as an insert or a component of a transport box or in packaging for bakery products. Currently, bakery products are transported in open packaging which are open to allow moisture to escape. However, this does not enable optimal and hygienic packaging of bakery products because the open bread boxes are exposed to environmental influences. When the felt insert according to the invention is employed, so called "sweating" of the bakery products can be prevented while hygienic packaging is provided at the same time. Since the absorber-containing layer is felted into the felt material according to the invention so that it cannot be lost, this also ensures that particles of the absorber polymer will not come into contact with the foodstuffs. Another type of use in the packaging industry represents the use in packaging for tobacco products which makes it possible to achieve an optimal regulation of moisture in the packaging.

In another type of application, the felt material according to the invention is used for pressure compensation elements in automotive technology, in housings, in photovoltaic technology, in electrical engineering and in the packaging industry. The pressure compensation elements which are manufactured from the felt material according to the invention are for example welded to the packaging or otherwise attached to the packaging so that the air in the packaging can be replaced by atmospheric air, while the content of the packaging is protected from water. In additional to conventional packagings, these pressure compensation elements are used for example in the top cover of beverage cups, fermentation bottles or container closures.

In another application in the packaging industry, the entire packaging, or a covering or an insert of the packaging is made of the felt material according to the invention. This is in particular useful when the content of the packaging needs to be securely protected from contact with water and when supplying of air or ventilation is desired.

When employed as a moisture binding filling material or in pillow materials, the felt material is used to regulate moisture or for dehumidification.

The felt material according to the invention or structural components thereof can be also used thanks to the moisture binding effect as functional elements that are employed for dehumidification or for climatic regulation for example in safety helmets or protective suits. Protective suits are worn for example by blast furnace workers, as clean room suits, as clothing for riding a motorcycle, or in clothing containing climatic membranes, when condensation water which is generated in suits, tents or insulation layers cannot escape to a sufficient extent. Good air circulation can be achieved with the felt material according to the invention, wherein the wearer of the protective suit is protected in a timely manner from penetrating moisture or fluids.

The felt material according to the invention can be constructed in such a way that it can serve as a tube providing moisture for plants or ventilation for plants. Such a tube or other corresponding forms of felt material are placed in soil or granular material and filled with a fluid. Moisture is delivered to the plants with the felt material which is at least partially permeable so that the level of the fluid in the irrigation equipment is lowered. Ventilation of the soil or of the granulate material is thus enabled also in areas which are no longer filled with the fluid thanks to the air permeability. In particular when a plant granulate is used, which is often used in closed pots, improved ventilation of the roots of the plant can be achieved in addition to simultaneous humidification.

Because it is suitable for removing condensation water, the felt material according to the invention is suitable for protective casings of electronic devices, such as in particular laptops, cell phones or cameras in which condensation water is collected as a result of fluctuating temperatures. Similarly, the felt material according to the invention or a structural component thereof can be employed in the device itself in order to transport condensation water from the device to the outside.

A further use for dehumidification is when the felt material is used as a cover for handles, for example handles of bags, suitcases, or tools for bicycles, wherein the moisture is absorbed as it is created and then removed at a later point so that the handle does not become unpleasantly moist when touched and so that slipping due to moisture is prevented.

The felt material according to the invention is further also suitable to be used as a sponge or a as an effective depository for an active ingredient. It can thus be used for example in a wound dressing for the delivery of medical drugs. Similarly, discharging of a detergent which is used in a cleaning sponge is also a conceivable application. The wound dressing is provided in another application for example with skincare active substances and with additional substances promoting healing. The felt material according to the invention then serves as a depository for this active ingredient or for this additional substance which is either integrated in such a form so that it is delivered directly, or through the contact with the fluid secreted from the wound or with other fluids, wherein the active ingredients are released and discharged outside. The felt material according to the invention is in this case for example used as a wound dressing with or without additives in a wound dressing under compression bandages, or as a textile addition in wound plasters or absorbent pads.

In another application in the medical field, the felt material according to the invention is used as an absorbent pad either in the dry form or in a pre-moistened form. The absorbent pad is used for example for heavily exuding wounds, with surgical wounds, with lymphatically induced wounds, with exulcerating tumors or with ulcus cruris. The absorbent pad manufactured with the felt material according to the invention absorbs moisture released by the wound and thus exerts a positive influence on the wound healing process. Alternatively, the absorbent pad delivers further active ingredients or additional substances to the wound and to the surrounding skin. With targeted absorption of moisture and delivery through the absorbent pad, the wound dressing need to be exchanged less frequently, which can also have a positive influence on the healing process and which can lead to a reduction in costs.

The felt material according to the invention can be also used in another application for the manufacturing of tampons, panty liners, nursing pads or other hygienic products. This includes also the use in customary incontinence products or diaper products.

Blankets made from and provided with the felt material according to the invention are also ideal as blankets for domestic animals, for example as blankets for horses or for transport of small animals. Sweat or urine discharged by the animal is absorbed by the blanket so that the animal does not sit in the wet spot and does not suffer in this manner.

The felt material according to the invention is used in wiper blades instead of or in addition to rubber plates, wherein it is also provided with an active ingredient which is delivered to the windshield.

The felt material according to the invention is further also employed as sealing or as a sealing insert for a colostomy bag or for its threads or connections. The felt material according to the invention is in this case equipped for example with active charcoal in order to filter the associated odors and to allow at the same time pressure equalization.

The filter material according to the invention can be used for insulation against cold in a number of applications. For example, it can be used in underwear, protective suits, socks, removable inner shoe liners, bandages, immobilization splints, corsets, wet suits, glasses for diving, goggles, hats and headbands, sheathing of cables, hose elements, covers of electrical devices such as for example cell phones, handle components, headphones, devices used for protection from noise, inflatable jackets, mattresses, neck cushions, pillows, blankets or other coverings and covers.

The felt material according to the invention is used in the construction field for example in order to absorb leaked water which can cause water damage in construction. The felt material according to the invention thus removes for example water absorbed in walls.

The felt material according to the invention is also used for example as a flat cover of an opening. In this case it is placed for example on a packaging or into a housing. Another possible application is to use it to provide a cover for surfaces in safety helmets which are equipped with openings. The flat cover is in this case designed either as a removable structural part or as a cover that is attached in a fixed manner to the object. The flat cover can be for example also covered with a material such as a laminate or a foil so that it is fixed on the object. In one embodiment, the flat cover is coated on one side with a plastic material, which is in the flowing state during the processing and which forms lateral surfaces extended over the felt, which are then connected with the object to be sealed.

The felt material according to the invention can be also employed as a structural component of a dehumidification system. It can thus be used for example in a condensation dryer to enable a quick absorption and binding of water and thus dehumidification of the environment.

It is also possible to manufacture from the material according to the invention cable sheathing, hose-shaped structures or hose sheathings. The sheathings can be produced for example by enveloping, wrapping or spraying the hose material on a textile to obtain the felt material according to the invention. When the felt material according to the invention is for example an outer layer of a fire hose, the material can be wetted with water by creating perforation in the media conducting the water, i.e. in the inner hose, so that a greater heat resistance of the fire extinguishing hose can be achieved.

The use of the felt material according to the invention in dust filters or dust masks makes it possible to realize specific filtering depending on the size of the particles to be filtered. Selective filtering can thus be realized depending on the type of the fibers, the degree of compaction and the thickness of the material. A key advantage of using the material in these protective masks or dust masks is moisture absorption which makes it possible to prevent sweating inside the mask. Dust particle are tightly bound to the sticky absorber when the absorber is swelling or swollen. After drying of the absorber polymer, the particles can be separated again, for example by shaking or with another type of mechanical treatment.

When the felt material according to the invention is employed inside safety helmets, goggles or protective masks, it prevents moisture from creating a mist on parts that are used for vision through the absorption of moisture. In addition, sensitive filter media in protective masks are protected from moisture and the functional life of the filter media is thus increased.

The moisture or water absorption of the felt material according to the invention is also used in order to absorb sweat or moisture obtained from objects which come into direct contact with the wearer. The felt material according to the invention is thus used to absorb sweat for example in belts, carrying straps, backpacks, shoulder straps, watch bands or similar items. This makes it possible to prevent generation of strong drenching or of long-lasting moisture. The safety of the wearer of the material can thus be improved and the risk of slipping can be decreased while the wearing comfort is increased. Sensitive materials, for example expensive leather, can be protected from moisture and sweat in this manner, so that the lifespan of the product is increased.

Another application of the felt material according to the invention is when it is used as a substrate material for plants, flower pots, terrariums or planters which can be formed with the substrate material or with the felt material according to the invention.

The felt material according to the invention is also used in boxes for watercolors. The felt material absorbs the water present in the box and prevents spilling of water. Since the humid content is bonding with the box, drying of colors is prevented at the same time.

The felt material according to the invention is also used in storage containers or storage bags for wet or moist objects. The felt material according to the invention removes moisture from the objects with the contained absorber polymers and conducts the moisture to the outside with a corresponding design. This is useful for example for storage containers for sport clothing, dental care products, dental braces or containers for dentures or braces, as well as for travel bags in which wet towels or other wet objects are transported.

The felt material according to the invention is also used as a structural component of packaging during the transport and storage of objects when a constant humidity is desired. This is applicable for example to transport and storage of car parts and metal parts, bulk materials such as cement or powders or construction materials, or of works of art or wood coverings. It can be also used as a structural component employed in pen caps against leaking of ink and drying of the writing pen, or against drying out of the pen and drying of gluing sticks or adhesives or other moisture releasing substances which lowers their quality due to evaporation of moisture such as shoe care products, deodorants and other cosmetic articles.

The felt material according to the invention is used as an insert in frozen packages which have the function of an ice pack. The felt material is moistened before freezing and it is stored so that the cold can be delivered in the unfrozen state to the relevant product. Alternatively, the felt material according to the invention serves for the absorption of leaking fluids and to prevent freezer burn.

In another embodiment, the felt material according to the invention is provided on one side with a felt layer which is created on one side partially or entirely from transparent fibers. The transparent fibers allow heat radiation (infrared radiation) to pass through so that the absorber containing layer is heated. The transparent fibers can in this case be designed in such a way that the heat radiation is not reflected again from the material so that the heating of the absorber-containing layer is additionally enhanced.

In another embodiment, the felt material according to the invention is used as an insert in hoods for removal of odors. Moisture containing odors is thus absorbed in a targeted manner. The material is additionally also filtered and it can be easily cleaned thanks to the fact that it is washable.

The felt material according to the invention can be employed thanks to its dehumidification properties, moisturizing and climatic regulation properties, as well as thanks to its barrier effect obtained with water and fluids in various structural components or as a material or partial material for a great number of objects and applications. This includes for example ironing board covers, board covers, supports for electronic structural components, absorbent pads in transport boxes or packaging, inner soles, filter material for inner soles glued on fur or leather, ski boots, skates, shoes, shoe parts, diver suits, protective suits provided with fire resistant coating, protective suits, umbrella stands, sleeping bags, covers for furniture, inkpads, paper products, landfill covers, greening of flat roofs, dams or dike constructions, items used for protection from flood, protection from fire, dental pads, surgical sponges, bathrooms for cats, transport boxes, child transport units, carrying straps, geotextiles, agricultural textiles, horse saddles, protective covers, bags for vacuum cleaners, cooling casings for beverage bottles, cooling casings for foodstuffs, drip catchers (droplet traps), bath mats, foot mats, scraper mats, sheathing of umbrellas, containers for glasses, hand rest surfaces, covering hoods for meals, door or window sealing products or absorbent pads for garbage containers.

In the agricultural field, the felt material according to the invention can be used for example so that seeds are contained in the felt material. The seeds can be for example inserted in strips. The felt material provided with the seeds is then installed in a vegetation substrate or on a vegetation substrate. This makes it possible to prevent the seeds from being blown away by wind or damaged by animals. The felt material according to the invention is also used to store water and it allows optimal watering. Optionally, other active ingredients having a positive influence on the seeds or the plants obtained from the seeds can be also introduced into the material. It is advantageous when the felt material according to the invention is in this case processed so that it includes natural fibers made of straw, hay or moss.

In another embodiment, the felt material according to the invention is used as a carrier or a culture medium for moss. The moss or moss spores are then provided with a covering layer which is provided on the carrier layer and/or absorber layer or attached to the felt material. The spores can be inserted into the felt material for example already during the manufacturing of the felt material so that the moss starts to grow as soon as it comes into contact with water. The material provided with the moss is suitable for roof or surface greening purposes, and it can be manufactured for example as a rolled product. The felt material according to the invention provided with moss can be also used for example for street edges, in sound protection barriers and on roofs, as well as for space dividers or for wall hangings in interior spaces or on terraces. Since the moss enables to reduce carbon dioxide, the felt material is particularly suitable for applications which are to improve air quality in urban areas.

A preferred application of the felt material according to the invention is when it is used as a cleaning device. The felt material according to the invention is in this case a structural component of a wiping mop, such as of mops that are used for wiping or other cleaning wipes which are optionally provided with an active ingredient or detergent. If the felt material is a blade of a mop, it will become hardened as a result of moisture, resulting in a higher abrasion which is at the same time accompanied by releasing of the active ingredients. A polishing effect is obtained as a result of a higher extent of abrasion, which is in particular suitable for parquet hardwood flooring. When it is provided with an active ingredient, the active ingredient is released in a uniform manner which results in uniform wetting of the surface to be cleaned. This provides a distinct improvement over conventional mops which lead to a different distribution of the detergent depending on the amount of the moisture that has been absorbed.

When the felt material according to the invention is used, a thermal bridge (cold gap) is prevented in many application fields with the regulation of moisture.

This makes it possible to achieve better insulation against cold. This is in particular suitable for use in clothing, in protective suits such as protective suits for melting surfaces, in construction materials, insulation materials or floor coatings.

The felt material according to the invention has the advantage that it provides permeability to air and thus enables air circulation and ventilation. Since the absorber polymers are tightly bonded in the fiber structure, the felt materials according to the invention can be cleaned or washed based on their mechanical strength. In addition, the structure of the felt material according to the invention has the advantage that the slippery or gel-like effect which results from the use of superabsorber materials in other areas can be avoided because the superabsorber is tightly integrated as a core into the material. The slippery or gel-like effect is created with other materials in which different layers of the absorber are mutually displaced during the wet state.

The felt material according to the invention and structural components manufactured with this material thus provide a number of advantages which are not provided by other comparable materials. The material according to the invention also makes it possible to combine characteristics for which it is otherwise necessary to link somewhat complicated connecting technologies in such a manner that they can be achieved by felt processing using needles in a processing which is based on the application of different layers, or on the processing of the layers. The material according to the invention permits simple handling as well as further processing. It is thus possible for example to deliver the material as a rolled product which is processed with conventional techniques such as punching, laser processing or hot punching for simple customization of the product. Unlike conventional absorber-containing materials, the material is characterized by a controlled volume increase. Protection against the leaking of the absorber-containing materials is ensured with the matrix of the fibers. The manufacturing is inexpensive because no special process or special machinery need to be employed in addition to the method according to the invention.

The invention will be now described by way of an example based on the attached figures, which show the following.

FIG. 1 shows a felt layer 2*a*, above which is arranged an absorber-containing layer 3. The absorber-containing layer consists of an absorber 4, which is built into a carrier material 5. Above the absorber-containing layer is arranged another felt layer 2*b*.

Figure 2:
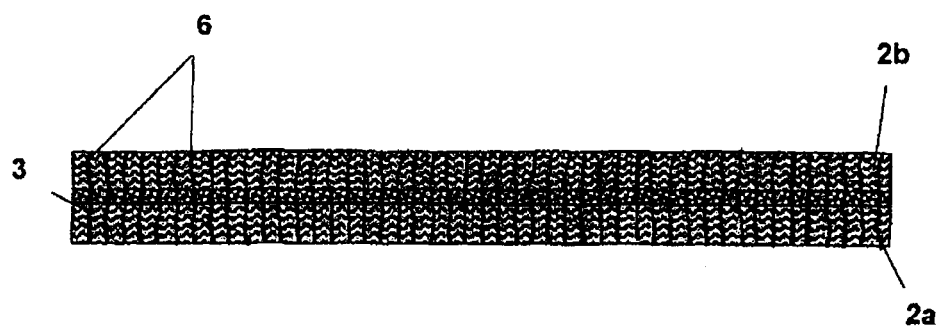
FIG. 2 shows the felt material from FIG. 1 in the felted state.

FIG. 2 shows the felt material from FIG. 2 after needling. The first felt layer and the second felt layer 2*b* can be here seen as being mutually connected with connecting fibers 6 which pass through the absorber-containing layer 3. The absorber is thus limited above and below by the first and the second felt layers, and on other sides by the connecting fibers 6.

Figure 3:
FIG. 3 shows another embodiment of the felt material according to the invention before felting.

FIG. 3 shows another embodiment of the felt material according to the invention before needling. The absorber-containing layer 3 is here arranged on a felt layer 2.

Figure 4:
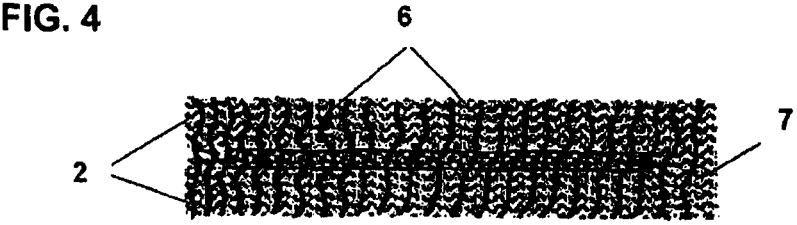
FIG. 4 shows the material from FIG. 3 after felting.

FIG. 4 shows the material from FIG. 3 after needling. The felt layer 2 was turned up over the absorber-containing layer 3 and it thus forms the edge seal 7.

The connecting fibers 6 are driven through the felt layer 2, which consists of the same felt material and the same felt layer, and through the absorber-containing layer.

Figure 5:
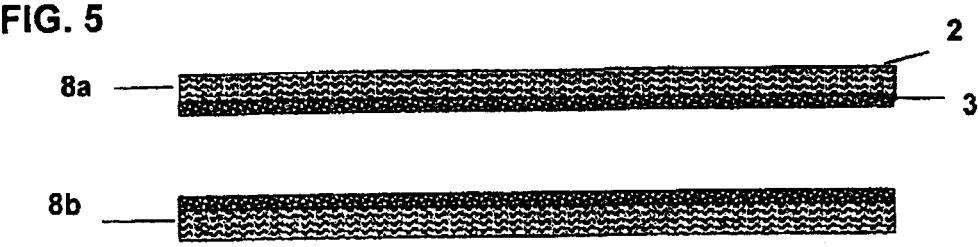
FIG. 5 shows another embodiment of the material according to the invention before felting.

FIG. 5 shows another embodiment of the felt material according to the invention before needling. In this embodiment, the absorber-containing felt layer 3 is a part of the felt layer 2 and it thus forms together with this layer a connecting layer 8*a*. Under the connecting layer 8*a* is arranged a second connecting layer 8*b*, wherein both sides of the connecting layers which are equipped with the absorber are facing each other.

Figure 6:
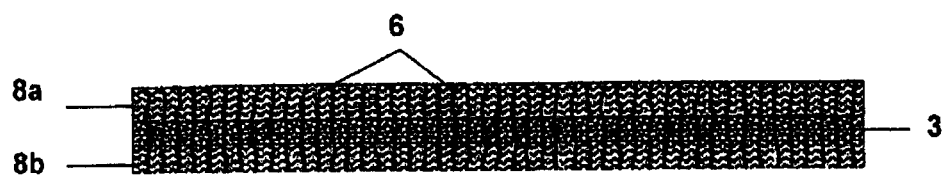
FIG. 6 shows the felt material from FIG. 5 after felting.

FIG. 6 shows the connecting layers 8*a* and 8*b* of FIG. 5 after needling. The absorber-containing regions of the connecting layers 8a and 8b are formed in the absorber-containing felt layers which are enclosed in the central region between the felt layers.

Figure 7:
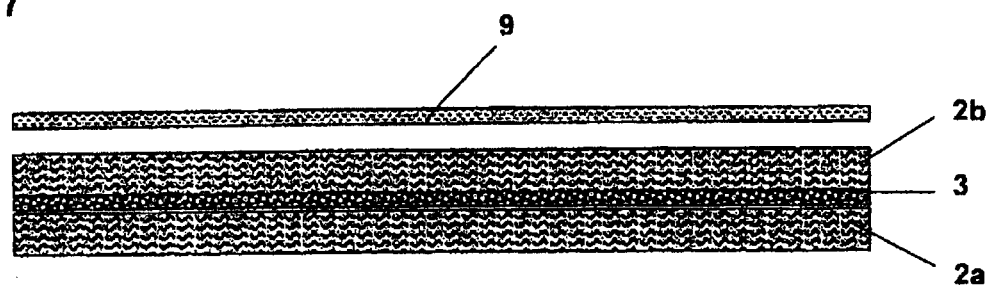
FIG. 7 shows another embodiment of the felt material according to the invention before felting.

FIG. 7 shown another embodiment of the felt material according to the invention wherein a covering layer 9 is arranged above the second felt layer 2b. The covering layer is formed here as a plastic film which is permeable to water and to air.

Figure 8:
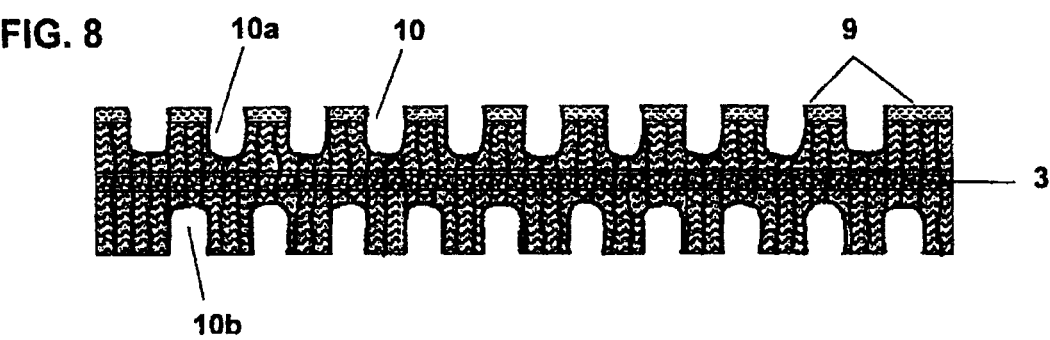
FIG. 8 shows an embodiment of the felt material according to the invention which is provided with perforations or openings.

FIG. 8 shows the material of FIG. 7 after needling and a follow-up treatment. The covering layer 9 is provided with perforations or openings 10 in the same manner as the felt layers. The perforations 10 are in this case created in the felt layer only to such a depth that one part of the felt layer remains above the absorber-containing layer 43. In the variant illustrated in the figure, the openings are arranged with a staggered design so that the opening 10a in the second felt layer is not located opposite the opening 10b in the first felt layer.

Figure 9:
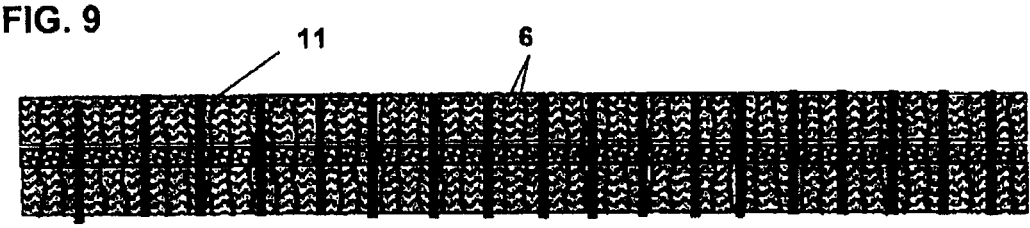
FIG. 9 shows an embodiment of the felt material according to the invention provided with sealing elements.

FIG. 9 shows another embodiment of the felt material according to the invention which is provided with locking elements 11 deployed in parallel as far from the connecting fibers as possible. The locking elements penetrate through the felt material arranged in stripes and divide the material into cells. When structural components are punched out and cut out from the felt material, at least a partial edge seal is provided with the locking elements 11.

Figure 10:
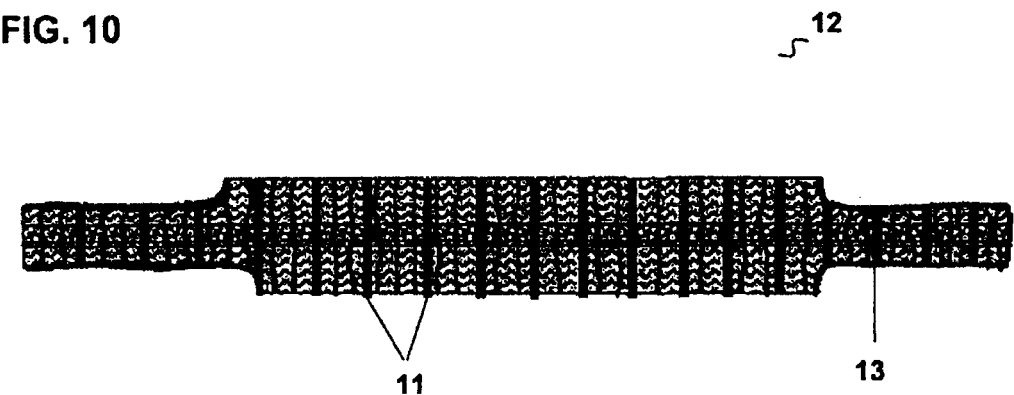
FIG. 10 shows a structural component having an edge seal made from the felt material according to FIG. 9.

FIG. 10 shows a structural component 11 which is manufactured from the felt material 9 of FIG. 9. The structural component is provided in addition to the locking elements 11 on both sides with connecting elements 13, which are suitable for connecting the structural component 12 to the object to be ventilated.

List Of Reference Symbols
1 felt material
2 felt layer
3 absorber-containing layer
4 absorber
5 carrier material
6 connecting fibers
7 edge seal
8 connecting layer
9 covering layer
10 openings
11 locking element
12 structural component
13 connecting elements

The invention claimed is:

1. Felt material having a blocking function for climatic regulation, comprising at least one felt layer and at least one fluid absorbing layer deployed at least in partial areas, characterized in that
at least one fluid absorbing layer is an absorber-containing layer,
at least one felt layer and the absorber-containing layer are mutually needled to each other,
an absorber in the absorber-containing layer is limited in its three-dimensional expansion by the felt layer(s) and/or by locking elements,
the absorber is a superabsorber polymer, or a swellable polymer selected from the group consisting of polyacrylic acid, polyacrylic acid copolymers, crosslinked sodium polyacrylate, casein, egg white and thermostatic elastomer composites, or a superabsorber polymer fiber,
the felt material is at least partial permeable to air in dry, open state, and
the felt material is closed when it comes into contact with a fluid, water or water vapor with the extension of the absorber, wherein the fluid transport through the felt material is limited or stopped by a swollen absorber.

2. Felt material according to claim 1, characterized in that the absorber layer is an absorber nonwoven material, an absorber polymer, an absorber, an absorber with a carrier material, an absorber granulate, an AirLaid material provided with absorbers, tissue or tissue-like material or absorber fibers.

3. The felt material according to claim 2, wherein the absorber nonwoven material is a nonwoven material with absorber polymers.

4. The felt material according to claim 1, characterized in that the felt material comprises at least in some areas three layers, wherein the first layer is a felt layer which has a layer made of absorber material arranged thereupon at least in partial areas, and another second felt layer arranged thereupon, while the three layers are at least partially mutually felted/needled with each other.

5. The felt material according to claim 1, characterized in that the absorber is limited in its three-dimensional extension at least partially by the connecting fibers between the felt layer(s).

6. The felt material according to claim 1, characterized in that the felt layer is made of synthetic, semi-synthetic, animal, mineral, metallic, vegetable, biodegradable fibers, hybrid fibers, rubber fibers or a mixture thereof.

7. The felt material according to claim 6, characterized in that the felt layer in addition to functional fibers contains or is mixed with a functional material.

8. The felt material according to claim 7, wherein the functional material is a phase change material (PCM)) or a shape memory material.

9. The felt material according to claim 4, characterized in that the first and the second felt layer are made of the same material, or that the second felt layers are made of different materials.

10. The felt material according to claim 4 characterized in that at least one felt layer and the absorber-containing layer and/or a second felt layer are needled with each other such that the felt material is permeable to air in dry state and permeable to air and non-permeable to water in the wet state.

11. The felt material according to claim 1, characterized in that the absorber-containing layer is constructed at least partially from fibers soluble in water or soluble in a detergent, or equipped with substances that are soluble in water or in a solvent, which are connected with the absorber polymer or which enclose the absorber polymer.

12. The felt material according to claim 4, characterized in that a covering layer is arranged on the first and/or potentially on the second felt layer, and that the second layer is potentially treated with a surface treatment.

13. The felt according to claim 12, characterized in that the covering layer is provided with perforations or openings, apertures, surface structures, tunnel structures, depressions, designated creasing locations or designated breaking locations and/or separating locations.

14. The felt according to claim 1, characterized in that the felt is provided with fragrances, dyes and/or active ingredients.

15. The felt according to claim 1, characterized in that the felt material additionally contains
molded parts, preferably parts molded from plastic or felt, which are felted with at least one felt layer or felted in the felt material and/or
locking elements, injected through the structure in advance in the direction of the connecting fibers.

16. The felt material according to claim 1, characterized in that in the felt material has a top side and a bottom side, wherein the top side and the bottom side have different properties.

17. Method for manufacturing a felt material comprising at least one felt layer and at least partially at least one absorber-containing layer, characterized in that
at least one absorber-containing layer is placed on one felt layer or between a first and second felt layers, and
the felt layer(s) and the absorber-containing layer are mutually needled with each other, or
one layer provided with precursors of an absorber polymer is placed on the felt layer and between the first and second felt layers, and
an absorber in the absorber-containing layer is a superpolymer absorber, or a polymer capable of swelling, selected from the group consisting of polyacrylic acid, polyacrylic acid copolymers, crosslinked sodium polyacrylate, casein, egg white and thermostatic elastomer composites, or a superabsorber polymer fiber,
the felt layers and precursor-containing layer and/or the second felt layer are mutually needled to each other and the polymerization to absorber polymer is ended during or after the felting procedure, wherein absorber in the absorber-containing layer is swollen when it comes into contact with a fluid, water or water vapor.

18. The method according to claim 17, characterized in that the absorber-containing layer is an absorber nonwoven fabric.

19. The method according to claim 17, characterized in that the absorber-containing layer is constructed from fibers which are soluble in water or in a detergent and which are connected with the absorber polymer or which enclose the absorber polymer.

20. The method according to claim 17, characterized in that the felt layer is made of synthetic, semi-synthetic, animal, mineral, metallic, vegetable, biodegradable fiber, rubber fibers hybrid fibers or a mixture thereof and/or the first and the second felt layer are made of the same material or different materials.

21. he method according to claim 17, characterized in that after needling, a covering layer is applied at least partially to the first and/or second layer and optionally, the covering layer is provided with perforations and openings when it is being applied or after the application.

22. The method according to claim 17, which further comprises a wet felting process step.

23. The method according to claim 17, characterized in that hollow needles are employed at least partially during the needling and felting process, through which the substances can be introduced during the felting process.

24. The method according to claim 17, characterized in that the felt material is provided at least partially with a surface treatment.

25. The method according to claim 17, characterized in that the absorber-containing layer is swollen or partially swollen before it is placed on the felt layer and that it is overfelted in the swollen or partially swollen state.

26. The method according to claim 17, characterized in that molded parts are positioned on the felt layer and or the absorber-containing layer which are felted during the needling with at least one of the layers.

27. The method according to claim 17, characterized in that plastic material is injected through the felt material in order to produce locking elements.

28. The method according to claim 27, characterized in that plastic material is injected through the felt material in order to produce locking elements in the direction of the connecting fibers.

29. The method according to claim 17, characterized in that the felt material produced thereby has a blocking function for climatic regulation, comprising
at least one felt layer and at least one fluid absorbing layer deployed at least in partial areas, characterized in that
at least one fluid absorbing layer is an absorber-containing layer,
at least one felt layer and the absorber-containing layer are mutually needled to each other,
the absorber is limited in its three-dimensional expansion by the felt layer(s) and/or by locking elements,
the felt material is at least partial permeable to air in dry, open state, and
the felt material is closed when it comes into contact with a fluid, water or water vapor with the extension of the absorber, wherein the fluid transport through the felt material is limited or stopped by the swollen absorber.

30. Structural component comprising a felt material having a blocking function for climatic regulation, comprising at least one felt layer and at least one fluid absorbing layer deployed at least in partial areas, characterized in that
at least one fluid absorbing layer is an absorber-containing layer,
at least one felt layer and the absorber-containing layer are mutually needled to each other,
an absorber in the absorber-containing layer is limited in its three-dimensional expansion by the felt layer(s) and/or by locking elements,
the absorber is a superpolymer absorber, or a polymer capable of swelling, selected from the group consisting of polyacrylic acid, polyacrylic acid copolymers, crosslinked sodium polyacrylate, casein, egg white and thermostatic elastomer composites, or a superabsorber polymer fiber,
the felt material is at least partial permeable to air in dry, open state, and
the felt material is closed when it comes into contact with a fluid, water or water vapor with the extension of the absorber, wherein the fluid transport through the felt material is limited or stopped by the swollen absorber.

31. The structural component according to claim 30, characterized in it is equipped with an edge seal.

32. Method for ventilating, dehumidifying, humidifying, sealing and/or climatic regulation of textile or non-textile objects, comprising the step of applying a felt material having a blocking function for climatic regulation, which felt material comprises at least one felt layer and at least one fluid absorbing layer deployed at least in partial areas, characterized in that
at least one fluid absorbing layer is an absorber-containing layer,
at least one felt layer and the absorber-containing layer are mutually needled to each other,
an absorber in the absorber-containing layer is limited in its three-dimensional expansion by the felt layer(s) and/or by locking elements,
the absorber is a superpolymer absorber, or a polymer capable of swelling, selected from the group consisting of polyacrylic acid, polyacrylic acid copolymers, crosslinked sodium polyacrylate, casein, egg white and thermostatic elastomer composites, or a superabsorber polymer fiber, the felt material is at least partial permeable to air in dry, open state, and the felt material is closed when it comes into contact with a fluid, water or water vapor with the extension of the absorber, wherein the fluid transport through the felt material is limited or stopped by the swollen absorber.

33. The method according to claim 32, wherein the felt material is formed as a component in a ventilation insert or ventilation surface and/or dehumidification insert or humidification insert adapted for textiles, clothing, shoes, inner soles of shoes, insert soles, lining, cushion materials, coverings, blankets, covers, tents, safety helmets, protective suits, protective covers, bandages, orthopedic articles, prostheses, containers, housings or bundles.

34. The method according to claim 32, wherein the felt material is formed as a component in a technical filter, seal, sealing tape, absorbent pad, sponge, bandage material, container for condensation water or for a cleaning device.

35. The method according to claim 32, wherein the felt material is formed as a component in a seal, ring seal, O-ring, washer, dehumidification insert in clothing, packaging or housings or structural component of housings.

* * * * *